US012747380B2

(12) United States Patent
Kawamoto et al.

(10) Patent No.: US 12,747,380 B2
(45) Date of Patent: Sep. 29, 2026

(54) GRANULATED PARTICLE FOR COLD STORAGE MATERIAL PARTICLE, COLD STORAGE MATERIAL PARTICLE, COLD STORAGE DEVICE, REFRIGERATOR, CRYOPUMP SUPERCONDUCTING MAGNET, NUCLEAR MAGNETIC RESONANCE IMAGING APPARATUS, NUCLEAR MAGNETIC RESONANCE APPARATUS, MAGNETIC FIELD APPLICATION TYPE SINGLE CRYSTAL PULLING APPARATUS, AND HELIUM RE-CONDENSING DEVICE

(71) Applicant: Niterra Materials Co., Ltd., Yokohama (JP)

(72) Inventors: Takahiro Kawamoto, Kawasaki Kanagawa (JP); Seina Taguchi, Yokohama Kanagawa (JP); Daichi Usui, Kawasaki Kanagawa (JP); Ryosuke Hiramatsu, Yokohama Kanagawa (JP); Hiroyasu Kondo, Yokohama Kanagawa (JP)

(73) Assignee: Niterra Materials Co., Ltd., Yokohama (JP)

( * ) Notice: Subject to any disclaimer, the term of this patent is extended or adjusted under 35 U.S.C. 154(b) by 374 days.

(21) Appl. No.: 18/584,152

(22) Filed: Feb. 22, 2024

(65) Prior Publication Data

US 2024/0287372 A1 Aug. 29, 2024

Related U.S. Application Data

(63) Continuation of application No. PCT/JP2022/032296, filed on Aug. 26, 2022.

(30) Foreign Application Priority Data

Aug. 30, 2021 (JP) ................................ 2021-139669

(51) Int. Cl.

*C09K 5/14* (2006.01)
*A61B 5/055* (2006.01)
*F28D 20/00* (2006.01)
*G01R 33/38* (2006.01)

(52) U.S. Cl.

CPC ............ *C09K 5/14* (2013.01); *F28D 20/0056* (2013.01); *G01R 33/3804* (2013.01); *A61B 5/055* (2013.01)

(58) Field of Classification Search

CPC .. A61B 5/055; C09K 5/02; C09K 5/14; F28D 20/0056; G01R 33/3804; H01F 1/017; Y02E 60/14

See application file for complete search history.

(56) References Cited

U.S. PATENT DOCUMENTS

| | | | |
|---|---|---|---|
| 3,878,119 A | 4/1975 | Nath | |
| 9,556,374 B2 | 1/2017 | Yamada et al. | |
| 2002/0026799 A1 | 3/2002 | Okamura et al. | |
| 2004/0013593 A1 | 1/2004 | Takagimi et al. | |
| 2015/0210911 A1 | 7/2015 | Yamada et al. | |
| 2017/0275176 A1 | 9/2017 | Yamada et al. | |
| 2019/0368785 A1 | 12/2019 | Kuriiwa et al. | |
| 2020/0248058 A1 | 8/2020 | Yanagitani et al. | |
| 2023/0279281 A1* | 9/2023 | Yamashita | C09K 5/14 252/71 |
| 2023/0303904 A1 | 9/2023 | Kawamoto et al. | |
| 2024/0384149 A1* | 11/2024 | Kawamoto | C01F 17/294 |
| 2026/0004958 A1* | 1/2026 | Hino | C09K 5/14 |

FOREIGN PATENT DOCUMENTS

| | | |
|---|---|---|
| JP | 2003-073661 A | 3/2003 |
| JP | 2003-213252 A | 7/2003 |
| JP | 2004-123884 A | 4/2004 |
| JP | 2005-160277 A | 6/2005 |
| JP | 2020-023713 A | 2/2020 |
| RU | 2293261 C2 | 2/2007 |
| WO | WO-2014/057657 A1 | 4/2014 |
| WO | WO-2016/047419 A1 | 3/2016 |
| WO | WO-2018/025581 A1 | 2/2018 |
| WO | WO-2018/117258 A1 | 6/2018 |
| WO | WO-2022/114045 A1 | 6/2022 |

OTHER PUBLICATIONS

International Search Report of International Patent Application No. PCT/JP2022/032296 dated Oct. 11, 2022, with partial English translation (7 pages).

US Non-Final Office Action for U.S. Appl. No. 18/323,288 dated Mar. 19, 2026 (17 pages).

* cited by examiner

*Primary Examiner* — Anthony J Green

(74) *Attorney, Agent, or Firm* — Foley & Lardner LLP

(57) ABSTRACT

A granulated particle for cold storage material particle according to an embodiment includes: a rare earth oxysulfide containing at least one rare earth element selected from the group consisting of Y, La, Ce, Pr, Nd, Sm, Eu, Gd, Tb, Dy, Ho, Er, Tm, Yb, and Lu, or a rare earth oxide containing at least one rare earth element selected from the group consisting of Y, La, Ce, Pr, Nd, Sm, Eu, Gd, Tb, Dy, Ho, Er, Tm, Yb, and Lu; and carbon having a concentration of 0.001 wt % or more and 50 wt % or less, in which the granulated particle has a relative density of 10% or more and 50% or less.

21 Claims, 8 Drawing Sheets

GRANULATED PARTICLE FOR COLD STORAGE MATERIAL PARTICLE, COLD STORAGE MATERIAL PARTICLE, COLD STORAGE DEVICE, REFRIGERATOR, CRYOPUMP SUPERCONDUCTING MAGNET, NUCLEAR MAGNETIC RESONANCE IMAGING APPARATUS, NUCLEAR MAGNETIC RESONANCE APPARATUS, MAGNETIC FIELD APPLICATION TYPE SINGLE CRYSTAL PULLING APPARATUS, AND HELIUM RE-CONDENSING DEVICE

CROSS-REFERENCE TO RELATED APPLICATION

This application is continuation application of, and claims the benefit of priority from Japanese Patent Application No. 2021-139669, filed on Aug. 30, 2021, and the International Application PCT/JP2022/032296, filed on Aug. 26, 2022, the entire contents of which are incorporated herein by reference.

FIELD

Embodiments described herein relate generally to a granulated particle for cold storage material particle, a cold storage material particle, a cold storage device, a refrigerator, a cryopump, a superconducting magnet, a nuclear magnetic resonance imaging apparatus, a nuclear magnetic resonance apparatus, a magnetic field application type single crystal pulling apparatus, and a helium re-condensing device.

BACKGROUND

In recent years, superconducting technologies have been remarkably developed, and it is necessary to develop compact and high-performance cryogenic refrigerators as the superconducting technologies are applied to expanding fields. The cryogenic refrigerators are required to be lightweight, compact, and highly thermally efficient. The cryogenic refrigerators have been put into practical use in various application fields A cryogenic refrigerator includes a cold storage device filled with a plurality of cold storage materials. For example, cold is generated by heat exchange between the cold storage material and helium gas passing through the cold storage device. For example, in a superconducting MRI apparatus, or in a cryopump or the like used in a semiconductor manufacturing device or the like, a refrigerator using a refrigeration cycle of a Gifford-McMahon (GM) type, a Stirling type, or a pulse tube type is used.

In addition, a high-performance refrigerator is also required for a magnetically levitated train in order to generate a magnetic force using a superconducting magnet. Furthermore, in recent years, a high-performance refrigerator has also been used in a superconducting magnetic energy storage (SMES), a magnetic field application type single crystal pulling apparatus for producing high-quality silicon wafers, or the like. In addition, it is also actively promoted to develop and practically apply a pulse tube refrigerator expected to have high reliability.

In the superconducting magnet, the MRI apparatus, and the like as described above, since liquid helium used evaporates, the supply of the liquid helium becomes a problem. In recent years, the helium depletion problem has become serious, and it is difficult to obtain helium, affecting the industry.

In order to reduce the consumption of liquid helium and reduce the burden of maintenance such as replenishment, helium re-condensing devices for re-condensing evaporated helium have been put into practical use, and the demand for the helium re-condensing devices has increased. The helium re-condensing device also uses a GM refrigerator or a pulse tube refrigerator that cools helium to a 4K-level temperature to liquefy the helium.

In a refrigerator, a working medium such as compressed helium (He) gas flows in one direction in a cold storage device filled with a cold storage material, and thermal energy thereof is supplied to the cold storage material. Then, the expanded working medium receives thermal energy from the cold storage material while flowing in the cold storage device in the opposite direction. As the recuperation effect is improved through such a process, thermal efficiency in the working medium cycle is improved, thereby achieving a lower temperature. In order to smoothly exchange thermal energy between the helium gas and the cold storage material, it is preferable that the cold storage material has a high thermal conductivity.

Here, as the specific heat per unit volume of the cold storage material filled in the cold storage device is higher, the thermal energy that can be stored in the cold storage material increases, so that the refrigeration capacity of the refrigerator is improved. Therefore, it is preferable to fill a cold storage material having a high specific heat at a low temperature on the low-temperature side of the cold storage device and fill a cold storage material having a high specific heat at a high temperature on the high-temperature side of the cold storage device.

A magnetic cold storage material has a high volume specific heat in a specific temperature range depending on its composition. Therefore, by combining magnetic cold storage materials having different compositions exhibiting different volume specific heats, the cold storage capacity is enhanced, and the refrigeration capacity of the refrigerator is improved.

In addition, as the thermal conductivity and the heat transfer coefficient of the cold storage material filled in the cold storage device are higher, the heat energy transfer efficiency is improved, and the efficiency of the refrigerator is improved.

In a conventional refrigerator, 4 K refrigeration has been achieved by filling metal cold storage material particles such as lead (Pb), bismuth (Bi), or tin (Sn) on a high-temperature side of a cold storage device, and filling metal-based magnetic cold storage material particles such as $Er_3Ni$, ErNi, or $HoCu_2$, on a low-temperature side of 20 K or less of the cold storage device.

In recent years, attempts have been made to improve the refrigeration capacity of the refrigerator by substituting some of the metal-based magnetic cold storage material particles with ceramic magnetic cold storage material particles having a high specific heat in a temperature range of 2 K to 10 K, such as $Gd_2O_2S$, $Tb_2O_2S$, $Dy_2O_2S$, $Ho_2O_2S$, and $GdAlO_3$.

The ceramic magnetic cold storage material particles are obtained through a multistage production process by mixing a raw material and a binder, granulating the mixture, degreasing the granule at several hundred degrees, sulfurizing the granule at several hundred degrees, and sintering the granule at one thousand and several hundred degrees. Therefore, if degreasing and sulfurization can be performed at a lower temperature than those in the related art, the production cost and the environmental burden can be reduced.

DETAILED DESCRIPTION

A granulated particle for cold storage material particle according to an embodiment includes: a rare earth oxysulfide containing at least one rare earth element selected from the group consisting of Y, La, Ce, Pr, Nd, Sm, Eu, Gd, Tb, Dy, Ho, Er, Tm, Yb, and Lu, or a rare earth oxide containing at least one rare earth element selected from the group consisting of Y, La, Ce, Pr, Nd, Sm, Eu, Gd, Tb, Dy, Ho, Er, Tm, Yb, and Lu; and carbon having a concentration of 0.001 wt % or more and 50 wt % or less, in which the granulated particle has a relative density of 10% or more and 50% or less.

Hereinafter, embodiments of the present invention will be described with reference to the drawings. In the following description, the same or similar members and the like will be denoted by the same reference signs, and the description of the members and the like once described may be appropriately omitted.

In the present specification, a cryogenic temperature means, for example, a temperature range in which a superconducting phenomenon can be industrially useful. For example, the cryogenic temperature is in a temperature range of 20 K or less.

First Embodiment

A granulated particle for cold storage material particle according to a first embodiment includes: a rare earth oxysulfide containing at least one rare earth element selected from the group consisting of yttrium (Y), lanthanum (La), cerium (Ce), praseodymium (Pr), neodymium (Nd), samarium (Sm), europium (Eu), gadolinium (Gd), terbium (Tb), dysprosium (Dy), holmium (Ho), erbium (Er), thulium (Tm), ytterbium (Yb), and lutetium (Lu), or a rare earth oxide containing at least one rare earth element selected from the group consisting of yttrium (Y), lanthanum (La), cerium (Ce), praseodymium (Pr), neodymium (Nd), samarium (Sm), europium (Eu), gadolinium (Gd), terbium (Tb), dysprosium (Dy), holmium (Ho), erbium (Er), thulium (Tm), ytterbium (Yb), and lutetium (Lu); and carbon having a concentration of 0.001 wt % or more and 50 wt % or less, and the granulated particle has a relative density of 10% or more and 50% or less.

Figure 1:
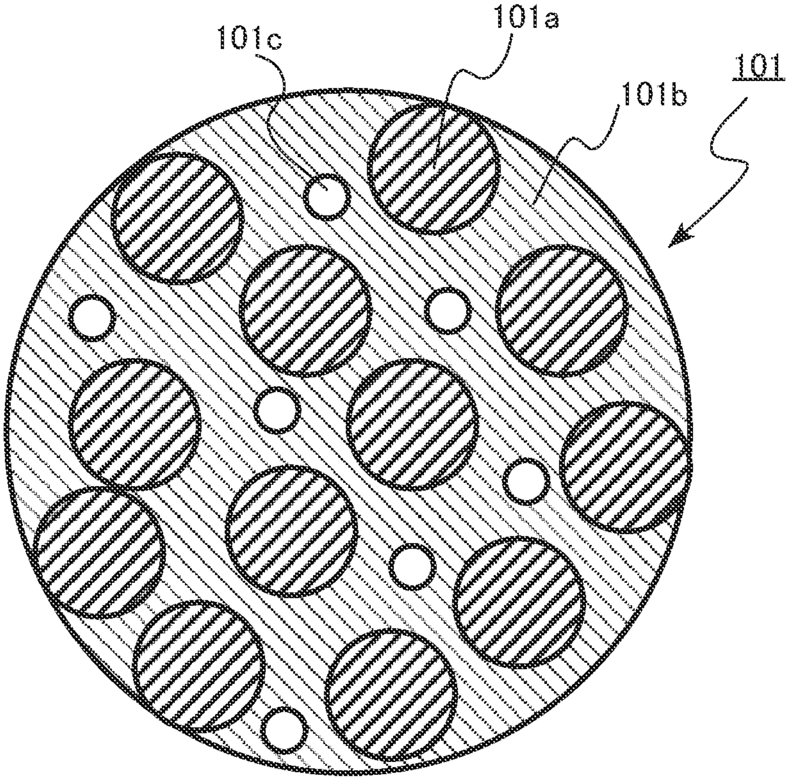
FIG. 1 is a schematic cross-sectional view of a granulated particle for cold storage material particle according to a first embodiment.

FIG. 1 is a schematic cross-sectional view of a granulated particle for cold storage material particle according to the first embodiment.

A granulated particle 101 for cold storage material particle according to the first embodiment is a granulated particle for producing a cold storage material particle. For example, a cold storage material particle is produced by subjecting the granulated particle 101 for cold storage material particle according to the first embodiment to a heat treatment for degreasing and a heat treatment for sintering. After the heat treatment for degreasing and before the heat treatment for sintering, the granulated particle 101 for cold storage material particle may be subjected to a heat treatment for sulfurization.

As illustrated in FIG. 1, the granulated particle 101 for cold storage material particle according to the first embodiment contains, for example, raw material powders 101*a*, a binder 101*b*, and voids 101*c*. The granulated particle 101 for cold storage material particle may contain, for example, a dispersion medium instead of the binder 101*b*. The granulated particle 101 for cold storage material particle may contain, for example, a gelling agent instead of the binder 101*b*. The raw material powders 101*a* may contain, for example, a sintering aid for promoting sintering at the time of producing the cold storage material particle.

The granulated particle 101 for cold storage material particle is formed by granulating the raw material powders 101*a*. The granulated particle 101 for cold storage material particle is formed, for example, by bonding the plurality of raw material powders 101*a* to each other with the binder 101*b*.

The granulated particle 101 for cold storage material particle is, for example, a gel. The granulated particle 101 for cold storage material particle is formed by, for example, gelling the plurality of raw material powders 101*a* using a gelling agent (gelling solution). For example, the raw material powders 101*a* are aggregated in a solidified state, losing independent mobility.

In a case where the granulated particle 101 for cold storage material particle is a gel, the granulated particle 101 for cold storage material particle contains, for example, raw material powders 101*a* and a dispersion medium. The dispersion medium contains, for example, a gelling agent. In a case where the granulated particle 101 for cold storage material particle is a gel, the granulated particle 101 for cold storage material particle contains, for example, raw material powders 101*a* and a gelling agent. The gelling agent gelled after gelling of the granulated particle 101 for cold storage material particle is also referred to as a gelling agent.

The raw material powder 101*a* contains a rare earth oxysulfide or a rare earth oxide. The rare earth oxysulfide contained in the raw material powder 101*a* contains at least one rare earth element selected from the group consisting of yttrium (Y), lanthanum (La), cerium (Ce), praseodymium (Pr), neodymium (Nd), samarium (Sm), europium (Eu), gadolinium (Gd), terbium (Tb), dysprosium (Dy), holmium (Ho), erbium (Er), thulium (Tm), ytterbium (Yb), and lutetium (Lu). The rare earth oxide contained in the raw material powder 101*a* contains at least one rare earth element selected from the group consisting of yttrium (Y), lanthanum (La), cerium (Ce), praseodymium (Pr), neodymium (Nd), samarium (Sm), europium (Eu), gadolinium (Gd), terbium (Tb), dysprosium (Dy), holmium (Ho), erbium (Er), thulium (Tm), ytterbium (Yb), and lutetium (Lu).

The rare earth oxysulfide contained in the raw material powder 101*a* is, for example, gadolinium oxysulfide or holmium oxysulfide. The rare earth oxysulfide contained in the raw material powder 101*a* is, for example, $Gd_2O_2S$, $Tb_2O_2S$, $Dy_2O_2S$, or $Ho_2O_2S$.

The rare earth oxide contained in the raw material powder 101*a* is, for example, gadolinium oxide or holmium oxide. The rare earth oxide contained in the raw material powder 101*a* is, for example, $Gd_2O_3$, $Tb_2O_3$, $Dy_2O_3$, or $Ho_2O_3$.

The raw material powder 101*a* may contain, for example, a carbonate, an oxide, a nitride, or a carbide containing a Group 1 element. The raw material powder 101*a* contains, for example, a carbonate, an oxide, a nitride, or a carbide containing a Group 2 element.

The raw material powder 101*a* may contain, for example, a carbonate, an oxide, a nitride, or a carbide containing an additive element. The additive element is at least one element selected from the group consisting of manganese (Mn), aluminum (Al), iron (Fe), copper (Cu), nickel (Ni), cobalt (Co), zirconium (Zr), yttrium (Y), and boron (B).

In a case where a sintering aid is contained as the raw material powder 101*a*, the sintering aid is, for example, an oxide. The sintering aid is, for example, an aluminum oxide (alumina), a magnesium oxide, an yttrium oxide, a zirconium oxide, or a boron oxide.

The binder 101*b* is an organic substance. The binder 101*b* is, for example, a resin. The binder 101*b* is, for example, polyvinyl alcohol, polyvinyl butyral, carboxymethyl cellulose, an acrylic resin, or polyethylene glycol.

In a case where a dispersion medium is contained in the granulated particle 101 for cold storage material particle, the dispersion medium is an organic substance. The dispersion medium is, for example, alginate. The dispersion medium is, for example, sodium alginate, ammonium alginate, or potassium alginate.

The granulated particle 101 for cold storage material particle has a relative density of 10% or more and 50% or less.

For example, when the relative density of the granulated particle 101 for cold storage material particle is low, the volume proportion of the raw material powders 101*a* in the granulated particle 101 for cold storage material particle is relatively small. When the relative density of the granulated particle 101 for cold storage material particle is low, a volume proportion of the binder 101*b*, the dispersion medium, or the voids 101*c* in the granulated particle 101 for cold storage material particle is relatively high.

On the other hand, when the relative density of the granulated particle 101 for cold storage material particle is high, a volume proportion of the raw material powders 101*a* in the granulated particle 101 for cold storage material particle is relatively high. When the relative density of the granulated particle 101 for cold storage material particle is high, a volume proportion of the binder 101*b*, the dispersion medium, or the voids 101*c* in the granulated particle 101 for cold storage material particle is relatively low.

The relative density of the granulated particle 101 for cold storage material particle can be calculated, for example, by dividing an average molding density obtained from 50 granulated particles by the true density of the constituent material. The average molding density of the 50 granulated particles is obtained by dividing a weight of the 50 particles by a volume of the 50 particles. The volume of the 50 particles can be calculated by adding up volumes of the respective particles obtained by assuming an equivalent circle diameter of each particle as a diameter of the particle.

In the calculation of the true density of the granulated particle 101 for cold storage material particle, first, a crystal phase of the raw material powders 101*a* constituting the granulated particle is identified by X-ray diffraction measurement. Then, a composition ratio of the raw material powders 101*a* constituting the granulated particle is obtained from Rietveld analysis or inductively coupled plasma atomic emission spectroscopy on an X-ray diffraction pattern. The true density of the granulated particle 101 for cold storage material particle can be calculated from the crystal phase of the raw material powders 101*a* and the composition ratio of the raw material powders 101*a*.

The granulated particle 101 for cold storage material particle has a particle diameter of, for example, 50 μm or more and 7 mm or less. The granulated particle 101 for cold storage material particle has an aspect ratio of, for example, 1 or more and 5 or less. The aspect ratio of the granulated particle 101 for cold storage material particle is a ratio of a major axis to a minor axis of the granulated particle 101 for cold storage material particle. The shape of the granulated particle 101 for cold storage material particle is, for example, spherical.

In the present specification, the particle diameter of the granulated particle 101 for cold storage material particle is an equivalent circle diameter. The equivalent circle diameter is a diameter of a perfect circle corresponding to an area of a figure observed in an image such as an optical microscope image or a scanning electron microscope image (SEM image). The particle diameter of the granulated particle 101 for cold storage material particle can be obtained, for example, by image analysis on an optical microscope image or an SEM image.

The granulated particle 101 for cold storage material particle contains carbon. The carbon contained in the granulated particle 101 for cold storage material particle has a concentration of 0.001 wt % or more and 50 wt % or less.

The carbon is contained in, for example, the binder 101*b* or the dispersion medium. For example, when the relative density of the granulated particle 101 for cold storage material particle is low, the concentration of carbon is relatively high. For example, when the relative density of the granulated particle 101 for cold storage material particle is high, the concentration of carbon is relatively low.

The granulated particle 101 for cold storage material particle contains, for example, a Group 1 element. The Group 1 element is, for example, at least one element selected from the group consisting of lithium (Li), sodium (Na), and potassium (K).

The Group 1 element is contained in, for example, the raw material powders 101*a*, the binder 101*b*, or the dispersion medium. The Group 1 element is derived from, for example, the gelling solution used in production of the granulated particle 101 for cold storage material particle.

The Group 1 element contained in the granulated particle 101 for cold storage material particle has a concentration of, for example, 0.001 atom % or more and 60 atom % or less.

The granulated particle 101 for cold storage material particle contains, for example, a Group 2 element. The Group 2 element is, for example, at least one element selected from the group consisting of magnesium (Mg), calcium (Ca), strontium (Sr), and barium (Ba).

The Group 2 element is contained in, for example, the raw material powders 101*a*, the binder 101*b*, or the dispersion medium. The Group 2 element is derived from, for example, the gelling solution used in production of the granulated particle 101 for cold storage material particle.

The Group 2 element contained in the granulated particle 101 for cold storage material particle has a concentration of, for example, 0.001 atom % or more and 60 atom % or less.

The granulated particle 101 for cold storage material particle contains, for example, an additive element that is at least one element selected from the group consisting of manganese (Mn), aluminum (Al), iron (Fe), copper (Cu), nickel (Ni), cobalt (Co), zirconium (Zr), yttrium (Y), and boron (B).

The additive element is contained in, for example, the raw material powders 101*a*, the binder 101*b*, or the dispersion medium. The additive element is derived from, for example, the gelling solution used in production of the granulated particle 101 for cold storage material particle.

The additive element contained in the granulated particle 101 for cold storage material particle has a concentration of, for example, 0.001 atom % or more and 60 atom % or less.

The detection of the element contained in the granulated particle 101 for cold storage material particle and the measurement of the atomic concentration of the element can also be performed, for example, by dissolving the granulated particle in a liquid, using inductively coupled plasma atomic emission spectroscopy (ICP-AES). It is also possible to use energy dispersive X-ray spectroscopy (EDX) or wavelength dispersive X-ray spectroscopy (WDX).

The method for producing the granulated particle for cold storage material particle according to the first embodiment is not particularly limited, but for example, the granulated particle can be produced by mixing raw material powders and a binder using a ball mill or the like to prepare a raw material mixture, and molding (granulating) the obtained raw material mixture into a granule by a rolling granulation method, a stirring granulation method, an extrusion method, a spraying method, a press molding method, or the like.

In the granulation method, the strength of the granulated particles is improved by adding the binder to adhere the raw material powders to each other. As the binder, for example, polyvinyl alcohol, polyvinyl butyral, carboxymethyl cellulose, an acrylic resin, polyethylene glycol, or the like can be used. The binder is added in an amount of, for example, 0.01 wt % or more and 40 wt % or less. For example, by increasing the amount of the binder, the fracture strength can be improved even though the relative density is low.

For the raw material powder, an oxide or an oxysulfide can be used. The type and the proportion of the oxide or the oxysulfide are adjusted in accordance with the target composition of the cold storage material particle.

A carbonate, an oxide, a nitride, or a carbide containing a Group 1 element, a Group 2 element, or an additive element can be used for the raw material powder. The additive element is at least one element selected from the group consisting of manganese (Mn), aluminum (Al), iron (Fe), copper (Cu), nickel (Ni), cobalt (Co), zirconium (Zr), yttrium (Y), and boron (B). By using a carbonate, an oxide, a nitride, or a carbide containing a Group 1 element, a Group 2 element, or an additive element for the raw material powder, a granulated particle for cold storage material particle containing the Group 1 element, the Group 2 element, or the additive element can be produced.

The raw material mixture may contain a sintering aid as a raw material powder. The sintering aid is, for example, an aluminum oxide (alumina), a magnesium oxide, an yttrium oxide, a zirconium oxide, or a boron oxide.

In the rolling granulation, for example, the relative density of the granulated particle for cold storage material particle can be changed by controlling a rotation speed of the granulator and a diameter of the granulator at the time of granulation. When the rotation speed is slow or the diameter of the granulator is small, rolling energy decreases, thereby reducing the relative density of the granulated particle for cold storage material particle.

In the production of the granulated particle for cold storage material particle according to the first embodiment, a slurry prepared by adding raw material powders to an alginic acid aqueous solution and mixing the raw material powders with the alginic acid aqueous solution may be added dropwise to a gelling solution, and the slurry may be gelled to granulate the slurry in a granular form. This method is a method in which particles are granulated by causing gelation through a crosslinking reaction by polyvalent metal ions contained in the gelling solution.

By changing the ratio between the raw material powders and the alginic acid aqueous solution, the relative density of the granulated particle for cold storage material particle can be changed. The weight ratio of the raw material powders to the alginic acid aqueous solution is, for example, 0.1 times or more and 20 times or less.

The granulated particle for cold storage material particle are solidified in a granular form by gelation of alginate. Therefore, the strength of the granulated particle, that is, the gelation strength, changes depending on the amount of alginate contained in the particle or the viscosity of the alginate aqueous solution. For example, by adjusting the viscosity of the alginate aqueous solution, the alginate can secure the raw material powders in the gel, maintain the strength of the granulated particle for cold storage material particle, and obtain granulated particle for cold storage material particle having a desired shape.

The slurry can be dropped into the gelling solution, for example, using a dropper, a burette, a pipette, a syringe, a dispenser, an inkjet, or the like. Hereinafter, the foregoing particle granulation method will be referred to as an alginic acid gel method.

In the alginic acid gel method, a particle diameter and an aspect ratio of the granulated particle for cold storage material particle can be changed by adjusting the viscosity of the slurry, the diameter of the discharge port at the time of dropping, or the distance between the tip of the discharge port and the liquid level of the gelling solution. The diameter of the discharge port is, for example, 50 μm or more and 3000 μm or less. The distance between the tip of the discharge port and the liquid level of the gelling solution is, for example, 0.1 mm or more and 1000 mm or less.

In a case where the dispenser is used for discharge, any one of an air-pulse dispenser, a plunger dispenser, and a piezo dispenser may be used as the device.

The inkjet is largely classified into a continuous type inkjet or an on-demand type inkjet as an ejection method, but any type of ejection method may be used. Further, the on-demand type inkjet is classified into a piezo type inkjet, a thermal type inkjet, and a valve type inkjet, but any one of the three types of inkjets may be used.

The slurry dropped into the gelling solution by a dropper, a burette, a pipette, a syringe, a dispenser, an inkjet, or the like is gelled by being held in the gelling solution. By gelling the slurry, a granulated particle containing the raw material powders of the cold storage material is formed. The time for which the slurry is held in the gelling solution is, for example, 10 minutes or more and 48 hours or less. If the gelation time is short, gelation will not sufficiently proceed, resulting in low strength of the granulated particle.

The alginic acid aqueous solution used in the alginic acid gel method is, for example, a sodium alginate aqueous solution, an ammonium alginate aqueous solution, or a potassium alginate aqueous solution. By using a sodium alginate aqueous solution or a potassium alginate aqueous solution containing a Group 1 element, sodium (Na) or potassium (K) can be contained in the granulated particle 101 for cold storage material particle. By using a mixed aqueous solution of a sodium alginate aqueous solution and a potassium alginate aqueous solution in the slurry, sodium (Na) and potassium (K) can be simultaneously contained in the granulated particle 101 for cold storage material particle.

The alginate has a concentration of, for example, 0.1 wt % or more and 5 wt % or less as an alginate aqueous solution. When the concentration of the alginate aqueous solution is lower than 0.1 wt %, a gel having sufficient strength cannot be generated, and a granulated particle for cold storage material particle cannot be obtained.

As the gelling solution, for example, a calcium lactate aqueous solution, a calcium chloride aqueous solution, a manganese (II) chloride aqueous solution, a magnesium sulfate aqueous solution, a beryllium sulfate aqueous solution, a strontium nitrate aqueous solution, a barium chloride aqueous solution, a barium hydroxide aqueous solution, an aluminum chloride aqueous solution, an aluminum nitrate aqueous solution, an aluminum lactate aqueous solution, an iron (II) chloride aqueous solution, an iron (III) chloride aqueous solution, a copper (II) chloride aqueous solution, a nickel (II) chloride aqueous solution, or a cobalt (II) chloride aqueous solution can be used.

By using a calcium lactate aqueous solution, a calcium chloride aqueous solution, a manganese (II) chloride aqueous solution, a magnesium sulfate aqueous solution, a beryllium sulfate aqueous solution, a strontium nitrate aqueous solution, a barium chloride aqueous solution, a barium hydroxide aqueous solution, an aluminum chloride aqueous solution, an aluminum nitrate aqueous solution, an aluminum lactate aqueous solution, an iron (II) chloride aqueous solution, an iron (III) chloride aqueous solution, a copper (II) chloride aqueous solution, a nickel (II) chloride aqueous solution, or a cobalt (II) chloride aqueous solution for the gelling solution, calcium (Ca), manganese (Mn), magnesium (Mg), beryllium (Be), strontium (Sr), barium (Ba), aluminum (Al), iron (Fe), copper (Cu), nickel (Ni), or cobalt (Co) can be contained in the granulated particle 101 for cold storage material particle.

In addition, by using an aluminum chloride aqueous solution, an aluminum nitrate aqueous solution, an aluminum lactate aqueous solution, an iron (II) chloride aqueous solution, an iron (III) chloride aqueous solution, a copper (II) chloride aqueous solution, a nickel (II) chloride aqueous solution, or a cobalt (II) chloride aqueous solution as the gelling solution, aluminum (Al), iron (Fe), copper (Cu), nickel (Ni), or cobalt (Co) can be contained in the granulated particle 101 for cold storage material particle.

Since gelation is caused through a crosslinking reaction by polyvalent metal ions contained in the gelling solution, in a case where an aqueous solution containing a Group 1 element is used for the slurry and an aqueous solution containing an element that forms polyvalent metal ions in the aqueous solution is used for the gelling solution, the amount of the Group 1 element contained in the particle and the amount of the element that forms polyvalent metal ions in the aqueous solution can be adjusted by adjusting a time for which the particle granulated by dropping the slurry into the gelling solution is immersed in the gelling solution.

The element that forms polyvalent ions in the aqueous solution is, for example, calcium (Ca), manganese (Mn), magnesium (Mg), beryllium (Be), strontium (Sr), barium (Ba), aluminum (Al), iron (Fe), copper (Cu), nickel (Ni), or cobalt (Co).

By using, as the gelling solution, a mixture of at least two kinds of aqueous solutions containing different metal elements selected from the group consisting of a calcium lactate aqueous solution, a calcium chloride aqueous solution, a manganese (II) chloride aqueous solution, a magnesium sulfate aqueous solution, a beryllium sulfate aqueous solution, a strontium nitrate aqueous solution, a barium chloride aqueous solution, a barium hydroxide aqueous solution, an aluminum chloride aqueous solution, an aluminum nitrate aqueous solution, an aluminum lactate aqueous solution, an iron (II) chloride aqueous solution, an iron (III) chloride aqueous solution, a copper (II) chloride aqueous solution, a nickel (II) chloride aqueous solution, and a cobalt (II) chloride aqueous solution, two or more kinds of elements forming polyvalent ions in the aqueous solutions can be contained in the granulated particle 101 for cold storage material particle.

Next, the function and effect of the granulated particle for cold storage material particle according to the first embodiment will be described.

A cold storage material particle is produced by subjecting the granulated particle for cold storage material particle to a heat treatment for degreasing and a heat treatment for sintering. For example, in a case where the granulated particle for cold storage material particle contains oxide raw material powders, the granulated particle for cold storage material particle may be subjected to a heat treatment for sulfurization after the heat treatment for degreasing and before the heat treatment for sintering.

By degreasing the granulated particle for cold storage material particle, a certain amount of an organic component contained in the binder or dispersion medium can be removed. For example, in a case where the raw material powder is an oxide, if degreasing is insufficient, the oxide is not sufficiently sulfurized, and as a result, a required amount of oxysulfide cannot be generated.

Furthermore, if the granulated particle for cold storage material particle is insufficiently degreased and the organic component remains in a large amount, the sintering reaction is also inhibited. When the sintering reaction is inhibited, the density of cold storage material particle after sintering decreases. When the density of the cold storage material particle decreases, the strength of the cold storage material particle decreases, and there is a risk that the cold storage material particle is broken during use in a refrigerator. In addition, when the sintering reaction is inhibited, the specific heat of the cold storage material particle after sintering decreases. When the specific heat of the cold storage material particle decreases, the performance of the refrigerator decreases.

On the other hand, if the granulated particle for cold storage material particle is degreased too much, an organic component necessary for ensuring strength will disappear. For this reason, the strength of the granulated particle after degreased may decrease, and the granulated particle may be cracked or chipped.

The granulated particle 101 for cold storage material particle according to the first embodiment has a relative density of 10% or more and 50% or less.

By setting the relative density of the granulated particle 101 for cold storage material particle to 50% or less, it is easy to remove an organic component contained in the binder or the dispersion medium during the heat treatment for degreasing. As a result, for example, the temperature of the heat treatment for degreasing can be reduced, or the time of the heat treatment for degreasing can be shortened. In addition, for example, the temperature of the heat treatment for sulfurization can be reduced, or the time of the heat treatment for sulfurization can be shortened. In addition, for example, the temperature of the heat treatment for sintering can be reduced, or the time of the heat treatment for sintering can be shortened. Consequently, the granulated particle 101 for cold storage material particle according to the first embodiment is capable of reducing the heat treatment temperature and the heat treatment time, thereby reducing a cost for manufacturing a cold storage material particle.

From the viewpoint of reducing the temperature of the heat treatment for degreasing, sulfurizing, or sintering, or from the viewpoint of reducing the time of the heat treatment for degreasing, sulfurizing, or sintering, the relative density of the granulated particle 101 for cold storage material particle is preferably 45% or less, and more preferably 40% or less.

When the relative density of the granulated particle for cold storage material particle is less than 10%, for example, the proportion of voids in the cold storage material particle increases, and the strength of the granulated particle for cold storage material particle decreases. When the strength of the granulated particle for cold storage material particle decreases, it is difficult to handle the granulated particle for cold storage material particle.

When the relative density of the granulated particle for cold storage material particle is less than 10%, the organic component may be excessively removed during the heat treatment for degreasing. When the organic component is excessively removed, the strength and the specific heat of the cold storage material particle produced decrease.

When the relative density of the granulated particle for cold storage material particle is less than 10%, for example, the relative density of the cold storage material particle produced decreases, and the specific heat of the cold storage material particle decreases. This is considered to be because the number of contact points between the raw material powders decreases and the sinterability of the cold storage material particle decreases.

By setting the relative density of the granulated particle 101 for cold storage material particle according to the first embodiment to 10% or more, the strength of the granulated particle 101 for cold storage material particle is maintained, and handling of the granulated particle for cold storage material particle is facilitated.

In addition, by setting the relative density of the granulated particle 101 for cold storage material particle to 10% or more, excessive removal of the organic component during the heat treatment for degreasing is suppressed. As a result, a decrease in strength and a decrease in specific heat of the produced cold storage material particle are suppressed.

In addition, by setting the relative density of the granulated particle 101 for cold storage material particle to 10% or more, the sinterability of the produced cold storage material particle is improved, and the specific heat of the cold storage material particle is improved.

From the viewpoint of maintaining the strength of the granulated particle 101 for cold storage material particle, the relative density of the granulated particle 101 for cold storage material particle is preferably 15% or more, and more preferably 20% or more. In addition, from the viewpoint of suppressing excessive removal of the organic component during the heat treatment for degreasing, the relative density of the granulated particle 101 for cold storage material particle is preferably 15% or more, and more preferably 20% or more. From the viewpoint of improving the sinterability of the produced cold storage material particle, the relative density of the granulated particle 101 for cold storage material particle is preferably 15% or more, and more preferably 20% or more.

The granulated particle 101 for cold storage material particle according to the first embodiment contains carbon having a concentration of 0.001 wt % or more and 50 wt % or less.

When the carbon concentration of the granulated particle for cold storage material particle is high, the strength of the granulated particle for cold storage material particle is improved. For example, when the carbon concentration of the granulated particle for cold storage material particle is less than 0.001 wt %, the strength of the granulated particle for cold storage material particle decreases and it is difficult to handle the granulated particle for cold storage material particle.

On the other hand, when the carbon concentration of the granulated particle for cold storage material particle is high, the thermal conductivity of the cold storage material particle produced from the granulated particle for cold storage material particle decreases. This is because carbon excessively remains at a crystal grain boundary of the produced cold storage material particle.

By setting the carbon concentration of the granulated particle 101 for cold storage material particle according to the first embodiment to 0.001 wt % or more, the strength of the granulated particle for cold storage material particle is improved. From the viewpoint of improving the strength of the granulated particle for cold storage material particle, the carbon concentration of the granulated particle 101 for cold storage material particle is preferably 0.01 wt % or more, and more preferably 0.1 wt % or more.

By setting the carbon concentration of the granulated particle 101 for cold storage material particle according to the first embodiment to 50 wt % or less, the thermal conductivity of the produced cold storage material particle is improved. From the viewpoint of improving the thermal conductivity of the produced cold storage material particle, the carbon concentration of the granulated particle 101 for cold storage material particle is preferably 10 wt % or less, and more preferably 5 wt % or less.

The granulated particle 101 for cold storage material particle according to the first embodiment preferably contains a Group 1 element having a concentration of 0.001 atom % or more and 60 atom % or less. As the granulated particle 101 for cold storage material particle contains a Group 1 element in the above-described concentration range, the sinterability of the produced cold storage material particle can be improved. As a result, for example, the strength and the specific heat of the produced cold storage material particle are improved.

From the viewpoint of improving the sinterability of the produced cold storage material particle, the concentration of the Group 1 element contained in the granulated particle 101 for cold storage material particle is more preferably 0.01 atom % or more and 30 atom % or less, and still more preferably 0.1 atom % or more and 10 atom % or less.

The granulated particle 101 for cold storage material particle according to the first embodiment preferably contains a Group 2 element having a concentration of 0.001 atom % or more and 60 atom % or less. As the granulated particle 101 for cold storage material particle contains a Group 2 element in the above-described concentration range, the sinterability of the produced cold storage material particle can be improved. As a result, for example, the strength and the specific heat of the produced cold storage material particle are improved.

From the viewpoint of improving the sinterability of the produced cold storage material particle, the concentration of the Group 2 element contained in the granulated particle 101 for cold storage material particle is more preferably 0.01 atom % or more and 30 atom % or less, and still more preferably 0.1 atom % or more and 10 atom % or less.

The granulated particle 101 for cold storage material particle according to the first embodiment preferably contains an additive element having a concentration of 0.001 atom % or more and 60 atom % or less, the additive element being at least one element selected from the group consisting of manganese (Mn), aluminum (Al), iron (Fe), copper (Cu), nickel (Ni), cobalt (Co), zirconium (Zr), yttrium (Y), and boron (B). As the granulated particle 101 for cold storage material particle contains an additive element in the above-described concentration range, the sinterability of the produced cold storage material particle can be improved. As a result, for example, the strength and the specific heat of the produced cold storage material particle are improved.

From the viewpoint of improving the sinterability of the produced cold storage material particle, the concentration of the additive element contained in the granulated particle 101 for cold storage material particle is more preferably 0.01 atom % or more and 30 atom % or less, and still more preferably 0.1 atom % or more and 10 atom % or less.

The granulated particle 101 for cold storage material particle according to the first embodiment preferably contains an aluminum oxide (alumina), a magnesium oxide, an yttrium oxide, a zirconium oxide, or a boron oxide. The oxide functions as a sintering aid. As the granulated particle 101 for cold storage material particle contains the above-described oxide, the sinterability of the produced cold storage material particle can be improved.

As described above, according to the first embodiment, it is possible to provide a granulated particle for cold storage material particle capable of reducing a cost for producing a cold storage material particle.

Second Embodiment

A cold storage material particle according to the second embodiment is obtained by sintering the granulated particle for cold storage material particle according to the first embodiment.

The cold storage material particle according to the second embodiment has a particle diameter of, for example, 50 μm or more and 5 mm or less. The cold storage material particle has an aspect ratio of, for example, 1 or more and 5 or less. The aspect ratio of the cold storage material particle is a ratio of a major axis to a minor axis of the cold storage material particle. The shape of the cold storage material particle is, for example, spherical. The cold storage material particle according to the second embodiment has, for example, a relative density of 90% or more. The relative density of the cold storage material particle according to the second embodiment is preferably 93% or more. The relative density of the cold storage material particle according to the second embodiment is more preferably 95% or more.

The cold storage material particle according to the second embodiment is a cold storage material particle obtained from the granulated particle for cold storage material particle according to the first embodiment. The cold storage material particle according to the second embodiment contains a rare earth oxysulfide or a rare earth oxide. The rare earth oxysulfide contained in the cold storage material particle contains at least one rare earth element selected from the group consisting of yttrium (Y), lanthanum (La), cerium (Ce), praseodymium (Pr), neodymium (Nd), samarium (Sm), europium (Eu), gadolinium (Gd), terbium (Tb), dysprosium (Dy), holmium (Ho), erbium (Er), thulium (Tm), ytterbium (Yb), and lutetium (Lu). In addition, the rare earth oxide contained in the cold storage material particle contains at least one rare earth element selected from the group consisting of yttrium (Y), lanthanum (La), cerium (Ce), praseodymium (Pr), neodymium (Nd), samarium (Sm), europium (Eu), gadolinium (Gd), terbium (Tb), dysprosium (Dy), holmium (Ho), erbium (Er), thulium (Tm), ytterbium (Yb), and lutetium (Lu).

The maximum value of the volume specific heat of the cold storage material particle according to the second embodiment in a temperature range of 2 K or more and 10 K or less is, for example, 0.5 J/(cm$^3$·K) or more.

The cold storage material particle according to the second embodiment contains, for example, a rare earth oxysulfide represented by the general formula $R_{2\pm0.1}O_2S_{1\pm0.1}$ (where R denotes at least one rare earth element selected from the group consisting of Y, La, Ce, Pr, Nd, Sm, Eu, Gd, Tb, Dy, Ho, Er, Tm, Yb, and Lu).

In the rare earth oxysulfide represented by the above general formula, the maximum value of the volume specific heat and the temperature indicating the maximum value of the volume specific heat vary depending on the selected rare earth element. Therefore, the specific heat characteristic of the rare earth oxysulfide can be adjusted by appropriately adjusting the proportion of the rare earth element. The rare earth element is, for example, at least one element selected from the group consisting of Gd, Tb, Dy, Ho, and Er. The rare earth element may include, for example, two or more kinds of rare earth elements.

The cold storage material particle according to the second embodiment contains, for example, a rare earth oxide represented by the general formula $R_{1\pm0.1}M_{1\pm0.1}O_{3\pm0.1}$ (where R denotes at least one element selected from the group consisting of Y, La, Ce, Pr, Nd, Sm, Eu, Gd, Tb, Dy, Ho, Er, Tm, Yb, and Lu, and M denotes at least one element selected from the group consisting of Al, Cr, Mn, and Fe).

In the rare earth oxide represented by the above general formula, the maximum value of the volume specific heat and the temperature indicating the maximum value of the volume specific heat vary depending on the selected rare earth element. Therefore, the specific heat characteristic of the rare earth oxide can be adjusted by appropriately adjusting the proportion of the rare earth element. The rare earth element is, for example, at least one element selected from the group consisting of Gd, Tb, Dy, Ho, and Er. The rare earth element may include, for example, two or more kinds of rare earth elements.

The cold storage material particle according to the second embodiment contains, for example, at least one element selected from the group consisting of aluminum (Al), magnesium (Mg), iron (Fe), copper (Cu), nickel (Ni), cobalt (Co), zirconium (Zr), and yttrium (Y). The element is, for example, an element derived from the sintering aid contained in the granulated particle 101 for cold storage material particle according to the first embodiment.

The cold storage material particle according to the second embodiment contains, for example, boron (B). The boron (B) is derived from, for example, the sintering aid contained in the granulated particle 101 for cold storage material particle according to the first embodiment.

The cold storage material particle according to the second embodiment contains a substance derived from the sintering aid of the granulated particle 101 for cold storage material particle according to the first embodiment as an oxide. The oxide is, for example, an aluminum oxide (alumina), a magnesium oxide, an yttrium oxide, a zirconium oxide, or a boron oxide.

The cold storage material particle according to the second embodiment contains, for example, 0.01 atom % or more and 20 atom % or less of at least one element selected from the group consisting of aluminum (Al), magnesium (Mg), iron (Fe), copper (Cu), nickel (Ni), cobalt (Co), zirconium (Zr), yttrium (Y), and boron (B).

The element constituting the sintering aid does not exhibit the specific heat characteristic. Therefore, when the amount of the element added exceeds 20 atom % in the cold storage material particle, the volume specific heat as the cold storage material particle decreases, resulting in a decrease in cold storage performance of a cold storage device and a decrease in refrigeration capacity of a refrigerator.

The cold storage material particle according to the second embodiment has, for example, a volume specific heat of 0.5 $J/(cm^3 \cdot K)$ or more in a temperature range of 2.5 K or more and 10 K or less. In addition, the cold storage material particle according to the second embodiment has, for example, a volume specific heat of 0.55 $J/(cm^3 \cdot K)$ or more in a temperature range of 2 K or more and 8 K or less. In addition, the cold storage material particle according to the second embodiment has, for example, a volume specific heat of 0.6 $J/(cm^3 \cdot K)$ or more in a temperature range of 4 K or more and 7 K or less.

The maximum value of the volume specific heat of the cold storage material particle according to the second embodiment in a temperature range of 2 K or more and 10 K or less is 0.5 $J/(cm^3 \cdot K)$ or more. As a result, the cold storage material particle according to the second embodiment has a high volume specific heat. Since the cold storage material particle according to the second embodiment has a high volume specific heat, a cold storage device filled with the cold storage material particle according to the second embodiment has a high cold storage performance, and a refrigerator equipped with the cold storage material particle according to the second embodiment exhibits a high refrigeration capacity.

The cold storage material particle according to the second embodiment has a particle diameter of, for example, 50 μm or more and 5 mm or less. The particle size of the cold storage material particle is preferably 1 mm or less, and more preferably 500 μm or less. When the particle size of the cold storage material particle is more than the above-described lower limit value, the packing density of cold storage material particles in the cold storage device is low, resulting in a reduction in pressure loss of the working medium such as helium, and an improvement in refrigeration performance of the refrigerator. On the other hand, when the particle size of the cold storage material particle is less than the above-described upper limit value, a distance from the surface of the cold storage material particle to the central portion of the particle is short, making it easy to convey heat transfer between the working medium and the cold storage material particle to the central portion of the cold storage material, resulting in an improvement in refrigeration performance of the refrigerator.

The particle diameter of the granulated particle for cold storage material particle is an equivalent circle diameter. The equivalent circle diameter is a diameter of a perfect circle corresponding to an area of a figure observed in an image such as an optical microscope image or a scanning electron microscope image (SEM image). The particle diameter of the granulated particle for cold storage material particle can be obtained, for example, by image analysis on an optical microscope image or an SEM image.

The cold storage material particle according to the second embodiment has, for example, a relative density of 90% or more. The relative density of the cold storage material particle according to the second embodiment is preferably 93% or more. The relative density of the cold storage material particle according to the second embodiment is more preferably 95% or more.

The relative density of the cold storage material particle according to the second embodiment can be calculated by dividing an average sintered density obtained from 50 cold storage material particles by the true density of the constituent material. The average sintered density of the 50 particles is determined by dividing weights of the 50 cold storage material particles by volumes of the 50 cold storage material particles. The volume of the 50 particles can be calculated by adding up volumes of the respective particles obtained by assuming an equivalent circle diameter of each particle as a diameter of the particle.

The crystal structure of the rare earth oxysulfide contained in the cold storage material particle according to the second embodiment is, for example, a $Ce_2O_2S$ type, and its space group is P-3m. The crystal structure can be confirmed by powder X-ray diffraction measurement, observation of an electron backscatter diffraction image using a scanning electron microscope, transmission electron microscopy, or the like.

The crystal structure of the rare earth oxide contained in the cold storage material particle according to the second embodiment is, for example, a perovskite type, and its space group is, for example, Pnma. In addition, the space group is, for example, Pm-3m. The crystal structure and the space group can be confirmed by powder X-ray diffraction measurement, observation of an electron backscatter diffraction image using a scanning electron microscope, transmission electron microscopy, or the like.

The cold storage material particle according to the second embodiment is produced by subjecting the granulated particle 101 for cold storage material particle according to the first embodiment to a heat treatment for degreasing and a heat treatment for sintering. For example, in a case where the granulated particle for cold storage material particle contains oxide raw material powders, the granulated particle for cold storage material particle may be subjected to a heat treatment for sulfurization after the heat treatment for degreasing and before the heat treatment for sintering.

The heat treatment for degreasing is performed, for example, in an air atmosphere. The temperature of the heat treatment for degreasing is, for example, 400° C. or more and 700° C. or less. The heat treatment time for degreasing is, for example, 30 minutes or more and 6 hours or less.

In a case where an oxide is used in the raw material powders 101*a* of the granulated particle 101 for cold storage material particle to produce a cold storage material particle containing an oxysulfide, the granulated particle 101 for cold storage material particle is sulfurized. In this case, the heat treatment is performed in a sulfurization atmosphere. The sulfurization atmosphere includes, for example, a gas containing a sulfur atom having a negative oxidation number, such as hydrogen sulfide ($H_2S$), carbon sulfide (CS), or methanethiol ($CH_3SH$). The temperature of the heat treatment for sulfurization is, for example, 400° C. or more and 600° C. or less. The time of the heat treatment for sulfurization is, for example, 1 hour or more and 5 hours or less.

The heat treatment for sintering the degreased granulated particle or the obtained oxysulfide is performed, for example, in an inert gas atmosphere. The temperature of the heat treatment is, for example, 1100° C. or more and 2000° C. or less. The temperature of the heat treatment is, for example, 1200° C. or more and 1800° C. or less. The time of the heat treatment is, for example, 1 hour or more and 48 hours or less.

When the granulated particle 101 for cold storage material particle contains a Group 1 element, a Group 2 element, or an additive element, the sintering temperature can be lowered by the sintering promotion effect, thereby shortening the sintering time. The additive element is at least one element selected from the group consisting of manganese (Mn), aluminum (Al), iron (Fe), copper (Cu), nickel (Ni), cobalt (Co), zirconium (Zr), yttrium (Y), and boron (B).

The heat treatment for sintering the granulated particle 101 for cold storage material particle containing a Group 1 element, a Group 2 element, or an additive element is performed, for example, in an inert gas atmosphere. The temperature of the heat treatment for sintering is, for example, 1000° C. or more and 2000° C. or less. The temperature of the heat treatment for sintering is, for example, 1100° C. or more and 1700° C. or less. The time of the heat treatment for sintering is, for example, 1 hour or more and 48 hours or less.

A cold storage material particle according to the second embodiment is produced by sintering the granulated particle 101 for cold storage material particle according to the first embodiment. Therefore, for example, the temperature of the heat treatment for degreasing can be reduced, or the time of the heat treatment for degreasing can be shortened. In addition, for example, the temperature of the heat treatment for sulfurization can be reduced, or the time of the heat treatment for sulfurization can be shortened. In addition, for example, the temperature of the heat treatment for sintering can be reduced, or the time of the heat treatment for sintering can be shortened. Consequently, a cost for producing a cold storage material particle according to the second embodiment is reduced.

In addition, a cold storage material particle according to the second embodiment is produced by sintering the granulated particle 101 for cold storage material particle according to the first embodiment. Therefore, for example, the organic component is sufficiently removed, the amount of residual carbon contained in the cold storage material particle is reduced, thereby improving the thermal conductivity of the cold storage material particle. Consequently, the performance of the refrigerator using the cold storage material particle according to the second embodiment is improved.

The cold storage material particle according to the second embodiment preferably has an aspect ratio of, for example, 1 or more and 5 or less. The aspect ratio of the cold storage material particle is more preferably, for example, 1 or more and 2 or less. When the aspect ratio of the cold storage material particle is less than the above-described upper limit value, when cold storage material particles are filled in the cold storage device, voids are uniform, improving the refrigeration performance of the refrigerator.

As described above, according to the second embodiment, it is possible to provide a cold storage material particle capable of reducing a production cost.

Third Embodiment

A cold storage device according to a third embodiment is a cold storage device filled with the plurality of cold storage material particles according to the second embodiment. In the cold storage device according to the third embodiment, for example, when a perimeter of a projection image of each of the plurality of filled cold storage material particles according to the second embodiment is denoted by L and an actual area of the projection image is denoted by A, the proportion of cold storage material particles having a circularity R of 0.5 or less, the circularity R being represented by $4\ \pi A/L^2$, is 5% or less.

The circularity R can be obtained by performing image processing on the shapes of the plurality of cold storage material particles using an optical microscope. The cold storage material particle having a circularity R of 0.5 or less represents a shape with irregularities on the surface or the like. When a plurality of cold storage material particles including such cold storage material particles in an amount of more than 5% are filled in the cold storage device, the porosity formed by the cold storage material particles in the cold storage device is uneven, and the filling property is unstable. Therefore, the cold storage performance deteriorates when the working medium flows in the cold storage device, or the cold storage material particles are moved or broken due to stress applied to the cold storage material particles at the time of filling the cold storage material particles or at the time of operating the refrigerator, generating fine particles, which causes voids to be clogged, thereby reducing the refrigeration performance and long-term reliability of the refrigerator. The proportion of cold storage material particles having a circularity R of 0.5 or less is preferably 2% or less, and more preferably 0%.

Fourth Embodiment

A refrigerator according to a fourth embodiment is a refrigerator including the cold storage device according to the third embodiment filled with the plurality of cold storage material particles according to the second embodiment. Hereinafter, explanations overlapping with those in the second embodiment and the third embodiment will be partially omitted.

Figure 2:
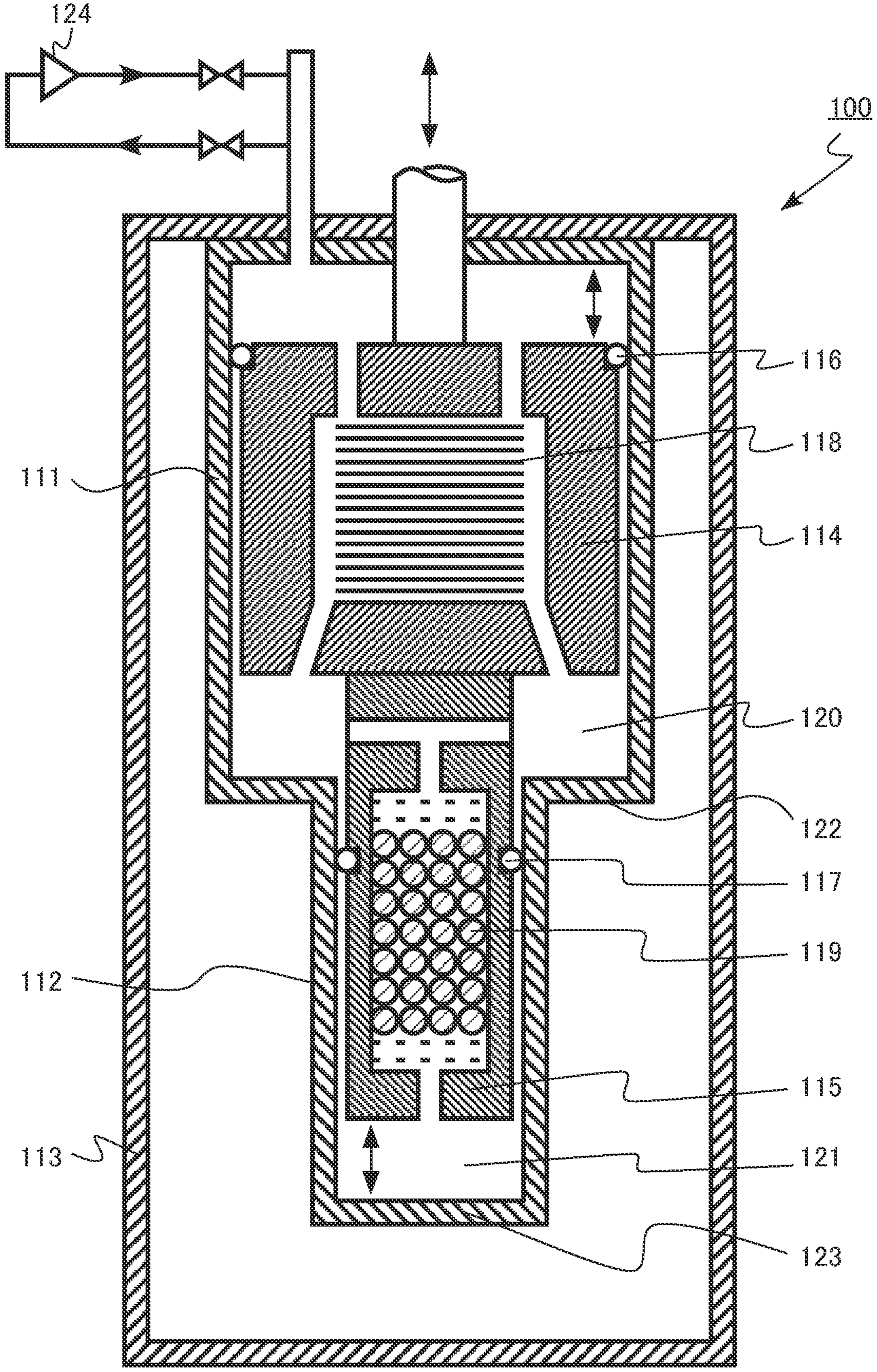
FIG. 2 is a schematic cross-sectional view illustrating a cold storage material particle according to a second embodiment and a configuration of a main part of a refrigerator according to a fourth embodiment.

FIG. 2 is a schematic cross-sectional view illustrating the cold storage material particle according to the second embodiment and a configuration of a main part of the refrigerator according to the fourth embodiment. FIG. 2 is a schematic cross-sectional view illustrating a configuration of a main part of a GM refrigerator which is an example of the refrigerator according to the fourth embodiment including the cold storage device according to the third embodiment filled with the plurality of cold storage material particles according to the second embodiment. The refrigerator according to the fourth embodiment is a two-stage cold storage cryogenic refrigerator 100 used for cooling a superconducting device or the like. The cold storage device filled with the plurality of cold storage material particles according to the second embodiment may be a Stirling type refrigerator or a pulse tube type refrigerator as well as the GM refrigerator.

The cold storage cryogenic refrigerator 100 (refrigerator) includes a first cylinder 111, a second cylinder 112, a vacuum container 113, a first cold storage device 114, a second cold storage device 115 (cold storage device), a first seal ring 116, a second seal ring 117, a first cold storage material 118, a second cold storage material 119 (cold storage material particles), a first expansion chamber 120, a second expansion chamber 121, a first cooling stage 122, a second cooling stage 123, and a compressor 124.

The cold storage cryogenic refrigerator 100 includes a vacuum container 113 in which a large-diameter first cylinder 111 and a small-diameter second cylinder 112 coaxially connected to the first cylinder 111 are installed. A first cold storage device 114 is disposed in the first cylinder 111 so as to be able to reciprocate. In the second cylinder 112, a second cold storage device 115, which is an example of the cold storage device according to the third embodiment, is disposed so as to be able to reciprocate.

A first seal ring 116 is disposed between the first cylinder 111 and the first cold storage device 114. A second seal ring 117 is disposed between the second cylinder 112 and the second cold storage device 115.

The first cold storage device 114 is filled with a first cold storage material 118 such as a Cu mesh. The second cold storage device 115 is filled with the plurality of cold storage material particles according to the second embodiment as a second cold storage material 119.

The second cold storage device 115 may be divided by a metal mesh material and include a plurality of cold storage material-filled layers. In a case where the second cold storage device 115 is divided into a plurality of filled layers, at least one filled layer is filled with a cold storage material particle group including the plurality of cold storage material particles according to the second embodiment, and is combined with, for example, at least one cold storage material particle group selected from a lead cold storage material particle group, a bismuth cold storage material particle group, a tin cold storage material particle group, a holmium copper cold storage material particle group, an erbium nickel cold storage material particle group, an erbium cobalt cold storage material particle group, and a gadolinium aluminum oxide cold storage material particle group.

In the combination of the cold storage materials, the cold storage materials are combined in such a manner that the peak temperature of specific heat is sequentially lowered, while a cold storage material having a higher peak temperature of specific heat is defined as a first cold storage material particle group, and a cold storage material having a lower peak temperature of specific heat is defined as a second cold storage material particle group.

In a case where the second cold storage device 115 is of a two-layer type, examples of the combination include a combination in which a holmium copper cold storage material particle group is used as a first cold storage material particle group, and the cold storage material particle group according to the second embodiment is used as a second cold storage material particle group. Further, in a case where the second cold storage device 115 is of a three-layer type, examples of the combination include a combination in which at least one cold storage material particle group selected from a lead cold storage material particle group, a bismuth cold storage material particle group, and a tin cold storage material particle group is used as a first cold storage material particle group, a holmium copper cold storage material particle group is used as a second cold storage material particle group, and the cold storage material particle group according to the second embodiment is used as a third cold storage material particle group.

The holmium copper cold storage material particle is preferably, for example, $HoCu_2$ or HoCu. The erbium nickel cold storage material particle is preferably, for example, ErNi or $Er_3Ni$.

Each of the first cold storage device 114 and the second cold storage device 115 has a working medium passage provided in a space in the first cold storage material 118 or the second cold storage material 119. The working medium is helium gas.

A first expansion chamber 120 is provided between the first cold storage device 114 and the second cold storage device 115. A second expansion chamber 121 is provided between the second cold storage device 115 and the distal end wall of the second cylinder 112. A first cooling stage 122 is provided at the bottom of the first expansion chamber 120. A second cooling stage 123 having a lower temperature than the first cooling stage 122 is formed at the bottom of the second expansion chamber 121. A high-pressure working medium is supplied from the compressor 124 to the above-described two-stage cold storage cryogenic refrigerator 100. The supplied working medium passes through the first cold storage material 118 filled in the first cold storage device 114 and reaches the first expansion chamber 120. Then, the working medium passes through the second cold storage material 119 filled in the second cold storage device 115 and reaches the second expansion chamber 121.

At this time, the working medium is cooled by supplying thermal energy to the first cold storage material 118 and the second cold storage material 119. The working medium passing through the first cold storage material 118 and the second cold storage material 119 expands in the first expansion chamber 120 and the second expansion chamber 121 to generate cold. Then, the first cooling stage 122 and the second cooling stage 123 are cooled.

The expanded working medium flows in the opposite direction through the first cold storage material 118 and the second cold storage material 119. The working medium is discharged after receiving thermal energy from the first cold storage material 118 and the second cold storage material 119. By improving the recuperation effect through such a process, the cold storage cryogenic refrigerator 100 is configured so that thermal efficiency in the working medium cycle is improved, thereby achieving a lower temperature.

As the cold storage device included in the refrigerator according to the fourth embodiment, the second cold storage device 115 is filled with the plurality of cold storage material particles according to the second embodiment as the second cold storage material 119. At least some of the second cold storage material 119 is the cold storage material particle according to the second embodiment.

With respect to the plurality of cold storage material particles according to the second embodiment, when a perimeter of a projection image of each of the cold storage material particles is denoted by L and an actual area of the projection image is denoted by A, it is preferable that the proportion of cold storage material particles having a circularity R of 0.5 or less, the circularity R being represented by $4\pi A/L^2$, is 5% or less.

In order to improve the refrigeration capacity of the refrigerator, it is preferable to improve the specific heat per unit volume of the cold storage material and to improve the thermal conductivity and the heat transfer coefficient of the cold storage material. The refrigerator according to the fourth embodiment includes a cold storage material or cold storage material particles which maintain a volume specific heat with improved thermal conductivity and heat transfer coefficient.

By using the refrigerator according to the fourth embodiment in a magnetically levitated train, the long-term reliability of the magnetically levitated train can be improved.

As described above, according to the fourth embodiment, a refrigerator having excellent characteristics can be realized by using cold storage material particles having excellent characteristics.

Fifth Embodiment

A cryopump according to a fifth embodiment includes the refrigerator according to the fourth embodiment. Hereinafter, explanations overlapping with those in the fourth embodiment will be partially omitted.

Figure 3:
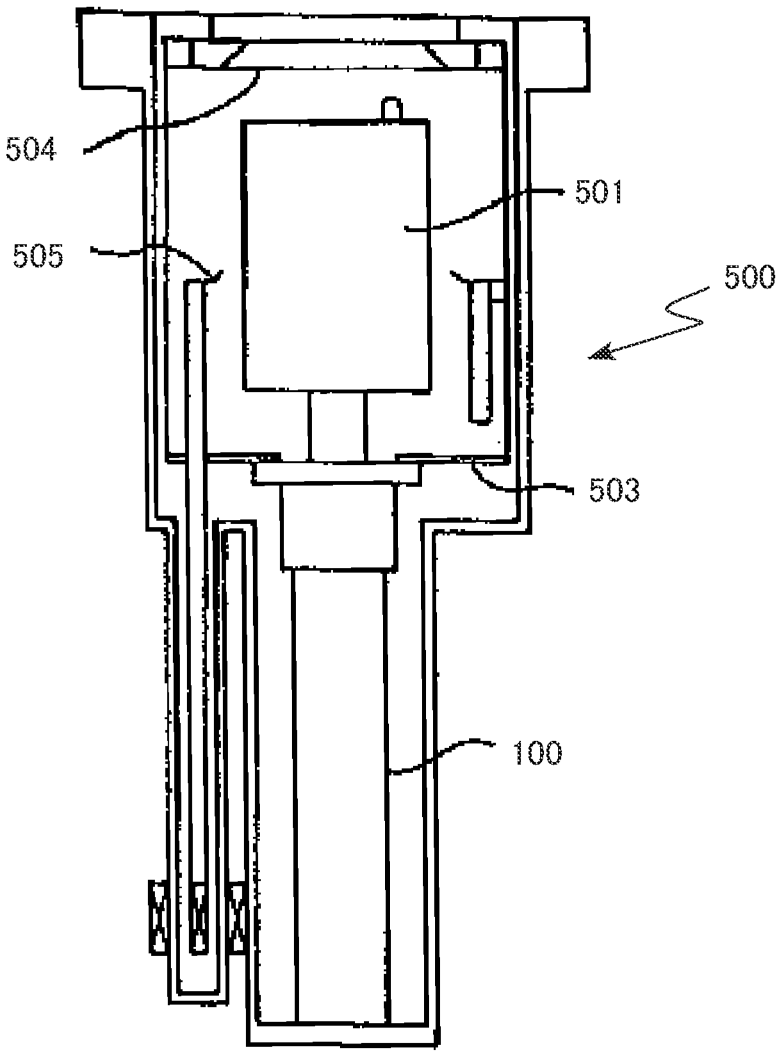
FIG. 3 is a cross-sectional view illustrating a schematic configuration of a cryopump according to a fifth embodiment.

FIG. 3 is a cross-sectional view illustrating a schematic configuration of a cryopump according to a fifth embodiment. The cryopump according to the fifth embodiment is a cryopump 500 including the cold storage cryogenic refrigerator 100 according to the fourth embodiment.

The cryopump 500 includes a cryopanel 501 that condenses or adsorbs gas molecules, a cold storage cryogenic refrigerator 100 that cools the cryopanel 501 to a predetermined cryogenic temperature, a shield 503 provided between the cryopanel 501 and the cold storage cryogenic refrigerator 100, a baffle 504 provided at an intake port, and a ring 505 that changes an exhaust speed of argon, nitrogen, hydrogen, or the like.

According to the fifth embodiment, a cryopump having excellent characteristics can be realized by using a refrigerator having excellent characteristics. In addition, by using the cryopump according to the fifth embodiment in a semiconductor manufacturing device or the like, the long-term reliability of the semiconductor manufacturing apparatus can be improved, and the number of times of maintenance of the semiconductor manufacturing device can be reduced. As a result, this contributes to an improvement in quality of a semiconductor to be manufactured and a reduction in manufacturing cost.

Sixth Embodiment

A superconducting magnet according to a sixth embodiment includes the refrigerator according to the fourth embodiment. Hereinafter, explanations overlapping with those in the fourth embodiment will be partially omitted.

Figure 4:
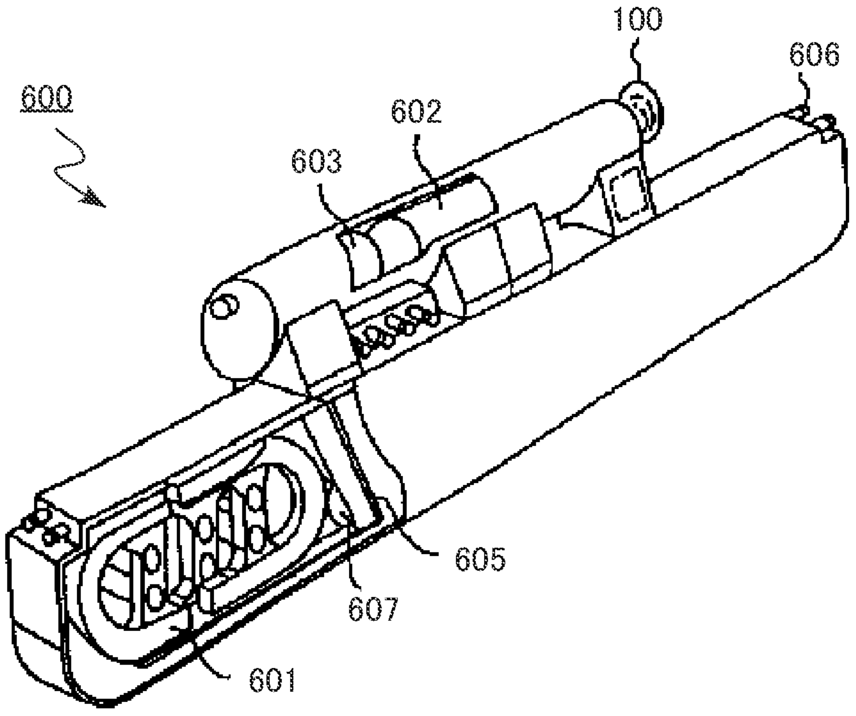
FIG. 4 is a perspective view illustrating a schematic configuration of a superconducting magnet according to a sixth embodiment.

FIG. 4 is a perspective view illustrating a schematic configuration of the superconducting magnet according to the sixth embodiment. The superconducting magnet according to the sixth embodiment is, for example, a superconducting magnet 600 for magnetically levitated train including the cold storage cryogenic refrigerator 100 according to the fourth embodiment.

The superconducting magnet 600 for magnetically levitated train includes a superconducting coil 601, a liquid helium tank 602 for cooling the superconducting coil 601, a liquid nitrogen tank 603 for preventing volatilization of liquid helium, a laminated heat insulating material 605, a power lead 606, a permanent current switch 607, and a cold storage cryogenic refrigerator 100.

According to the fifth embodiment, a superconducting magnet having excellent characteristics can be realized by using a refrigerator having excellent characteristics.

Seventh Embodiment

A nuclear magnetic resonance imaging apparatus according to a seventh embodiment includes the refrigerator according to the fourth embodiment. Hereinafter, explanations overlapping with those in the fourth embodiment will be partially omitted.

Figure 5:
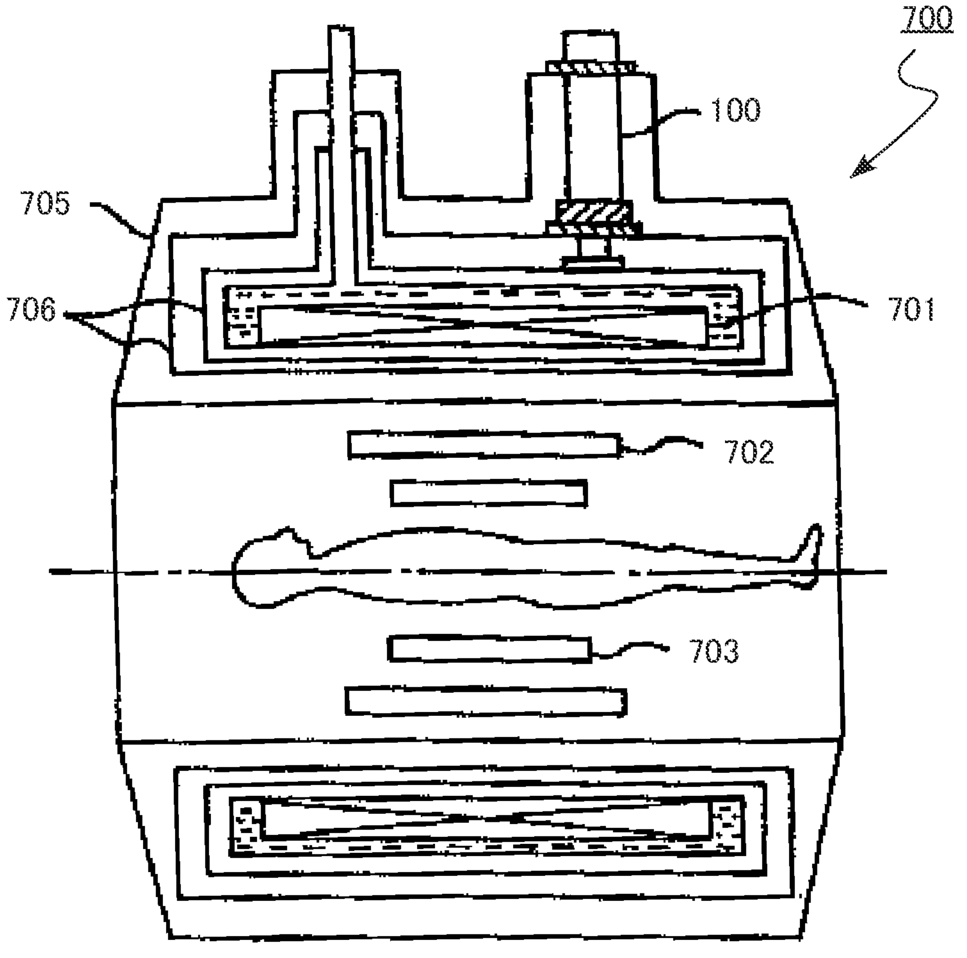
FIG. 5 is a cross-sectional view illustrating a schematic configuration of a nuclear magnetic resonance imaging apparatus according to a seventh embodiment.

FIG. 5 is a cross-sectional view illustrating a schematic configuration of the nuclear magnetic resonance imaging apparatus according to the seventh embodiment. The nuclear magnetic resonance imaging (MRI) apparatus according to the seventh embodiment is a nuclear magnetic resonance imaging apparatus 700 including the cold storage cryogenic refrigerator 100 according to the fourth embodiment.

The nuclear magnetic resonance imaging apparatus 700 includes a superconducting static magnetic field coil 701 that applies a spatially uniform and temporally stable static magnetic field to a human body, a correction coil that corrects nonuniformity of the generated magnetic field although not illustrated, a gradient magnetic field coil 702 that gives a magnetic field gradient to a measurement region, a radio wave transmission/reception probe 703, a cryostat 705, and a radiation adiabatic shield 706. In addition, the cold storage cryogenic refrigerator 100 is used for cooling the superconducting static magnetic field coil 701.

According to the seventh embodiment, a nuclear magnetic resonance imaging apparatus having excellent characteristics can be realized by using a refrigerator having excellent characteristics.

Eighth Embodiment

A nuclear magnetic resonance apparatus according to an eighth embodiment includes the refrigerator according to the fourth embodiment. Hereinafter, explanations overlapping with those in the fourth embodiment will be partially omitted.

Figure 6:
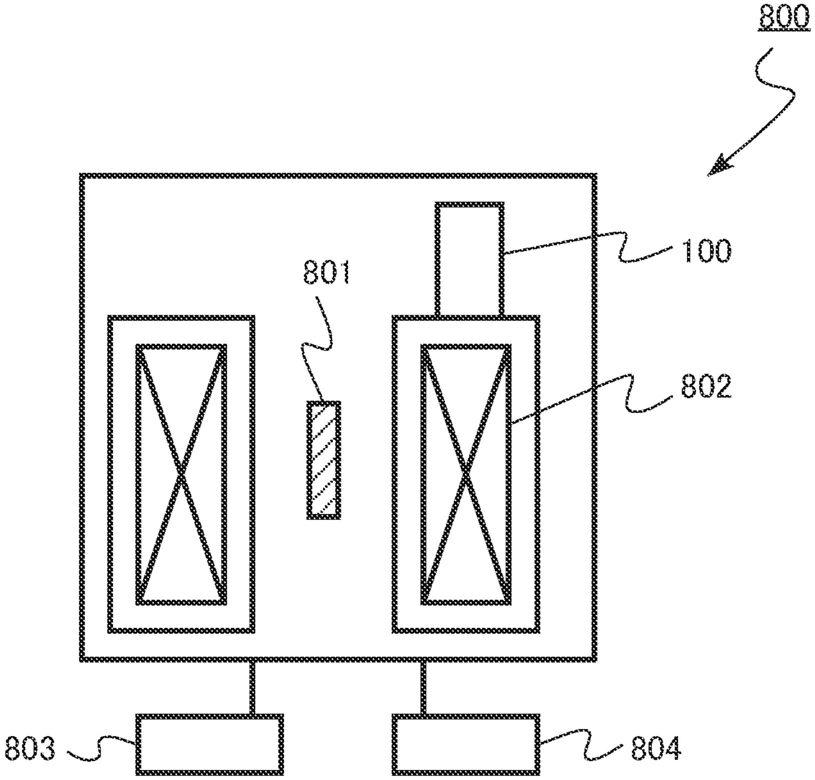
FIG. 6 is a cross-sectional view showing a schematic configuration of a nuclear magnetic resonance apparatus of an eighth embodiment.

FIG. 6 is a cross-sectional view illustrating a schematic configuration of the nuclear magnetic resonance apparatus according to the eighth embodiment. The nuclear magnetic resonance (NMR) apparatus according to the eighth embodiment is a nuclear magnetic resonance apparatus 800 including the cold storage cryogenic refrigerator 100 according to the fourth embodiment.

The nuclear magnetic resonance apparatus 800 includes a superconducting static magnetic field coil 802 that applies a magnetic field to a sample such as an organic substance placed in a sample tube 801, a high frequency oscillator 803 that applies a radio wave to the sample tube 801 in the magnetic field, and an amplifier 804 that amplifies an induced current generated in a coil that is not illustrated around the sample tube 801. In addition, the nuclear magnetic resonance apparatus 800 includes a cold storage cryogenic refrigerator 100 that cools the superconducting static magnetic field coil 802.

According to the eighth embodiment, a nuclear magnetic resonance apparatus having excellent characteristics can be realized by using a refrigerator having excellent characteristics.

Ninth Embodiment

A magnetic field application type single crystal pulling apparatus according to a ninth embodiment includes the refrigerator according to the fourth embodiment. Hereinafter, explanations overlapping with those in the fourth embodiment will be partially omitted.

Figure 7:
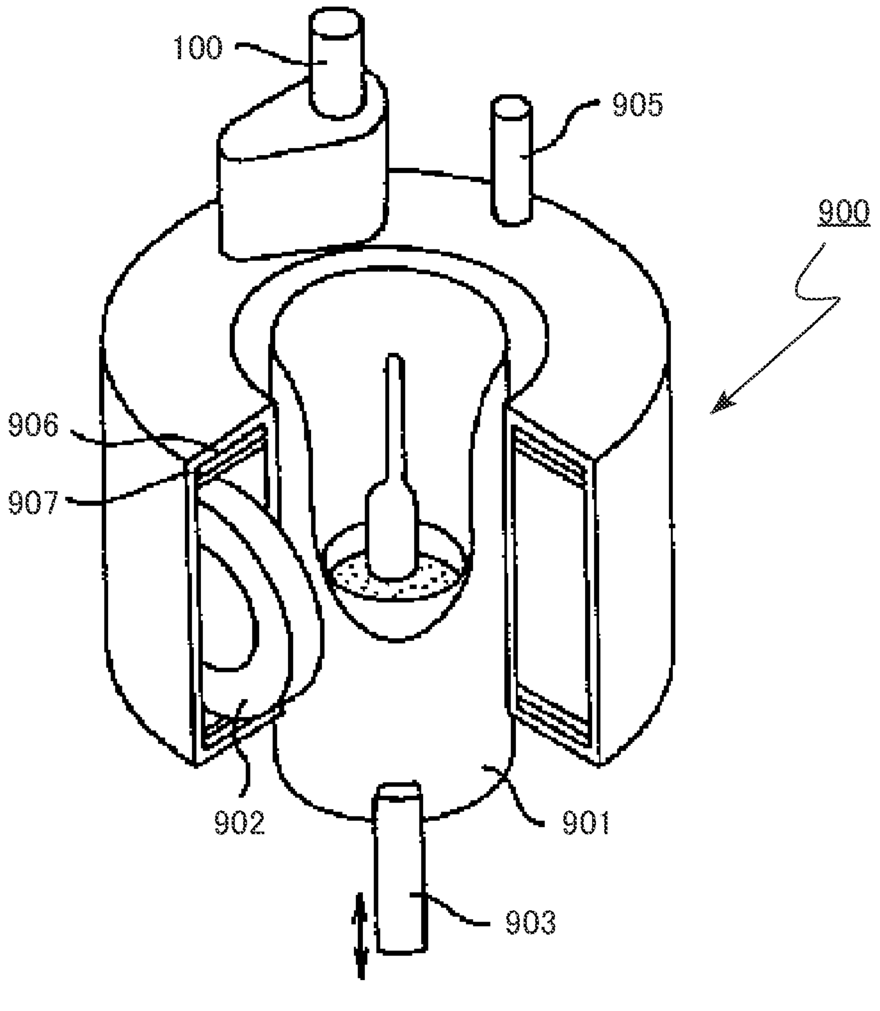
FIG. 7 is a perspective view illustrating a schematic configuration of a magnetic field application type single crystal pulling apparatus according to a ninth embodiment.

FIG. 7 is a perspective view illustrating a schematic configuration of the magnetic field application type single crystal pulling apparatus according to the ninth embodiment. The magnetic field application type single crystal pulling apparatus according to the ninth embodiment is a magnetic field application type single crystal pulling apparatus 900 including the cold storage cryogenic refrigerator 100 according to the fourth embodiment.

The magnetic field application type single crystal pulling apparatus 900 includes a single crystal pulling unit 901 having a raw material melting crucible, a heater, a single crystal pulling mechanism, etc., a superconducting coil 902 that applies a static magnetic field to a raw material melt, a lifting mechanism 903 of the single crystal pulling unit 901, a current lead 905, a heat shield plate 906, and a helium container 907. In addition, the cold storage cryogenic refrigerator 100 is used for cooling the superconducting coil 902.

According to the ninth embodiment, a magnetic field application type single crystal pulling apparatus having excellent characteristics can be realized by using a refrigerator having excellent characteristics.

Tenth Embodiment

A helium re-condensing device according to a tenth embodiment includes the refrigerator according to the fourth embodiment. Hereinafter, explanations overlapping with those in the fourth embodiment will be partially omitted.

Figure 8:
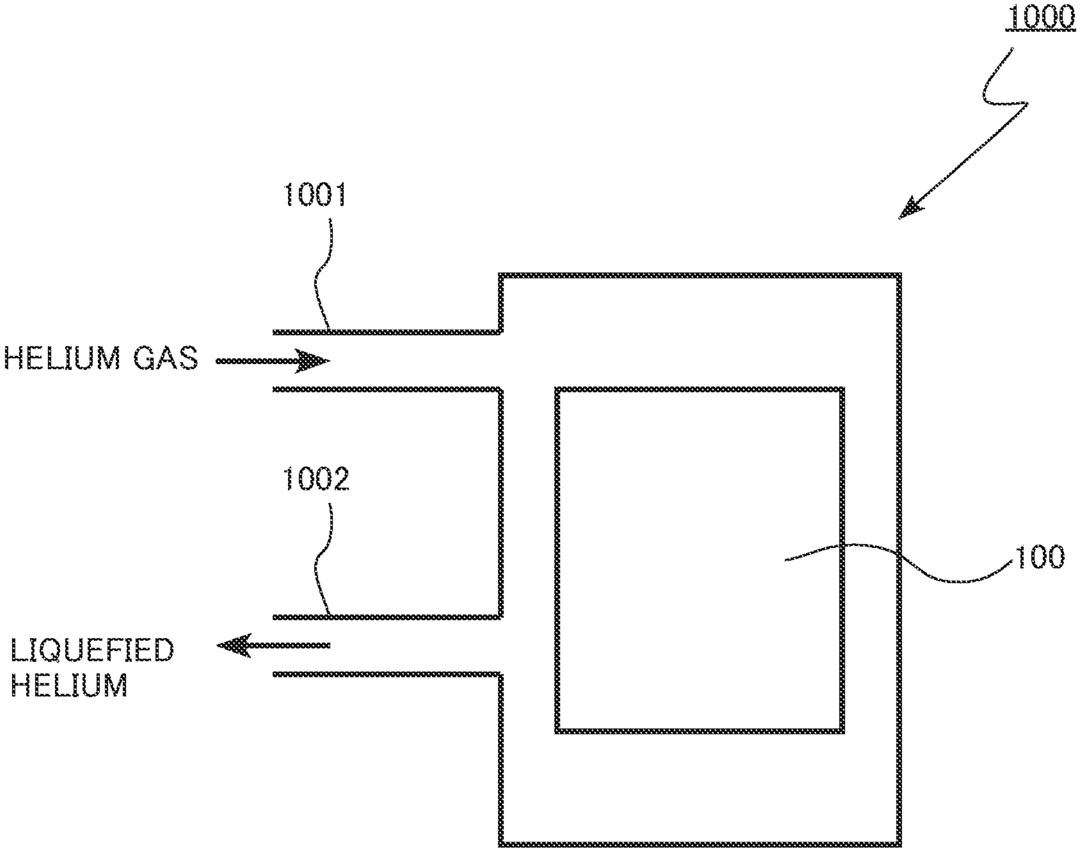
FIG. 8 is a schematic diagram illustrating a schematic configuration of a helium re-condensing device according to a tenth embodiment.

FIG. 8 is a schematic diagram illustrating a schematic configuration of the helium re-condensing device according to the tenth embodiment. The helium re-condensing device according to the tenth embodiment is a helium re-condensing device 1000 including the cold storage cryogenic refrigerator 100 according to the fourth embodiment.

The helium re-condensing device 1000 includes a cold storage cryogenic refrigerator 100, an evaporation pipe 1001, and a liquefaction pipe 1002.

The helium re-condensing device 1000 can re-condense helium gas into liquid helium which is evaporated from a device using liquid helium or a liquid helium device. The device using liquid helium may be a superconducting magnet, an nuclear magnetic resonance (NMR) device, a nuclear magnetic resonance imaging (MRI) device, or a physical property measurement system (PPMS). The liquid helium device may be included in a device using a superconducting magnet such as a magnetic property measurement system or the like.

The helium gas is introduced from a liquid helium device that is not illustrated into the helium re-condensing device 1000 through the evaporation pipe 1001. The helium gas is cooled to 4 K equal to or lower than a temperature for liquefaction of helium by the cold storage cryogenic refrigerator 100. The condensed and liquefied liquid helium returns to the liquid helium device through the liquefaction pipe 1002.

According to the tenth embodiment, a helium re-condensing device having excellent characteristics can be realized by using a refrigerator having excellent characteristics.

EXAMPLES

Hereinafter, examples of the granulated particle for cold storage material particle according to the first embodiment and the cold storage material particle according to the second embodiment, comparative examples, and results of evaluation thereof will be described.

Example 1

$Gd_2O_3$ powders were mixed and pulverized in a ball mill for 24 hours to prepare a raw material mixture. Next, the obtained raw material mixture was dried and then granulated using a tumbling granulator to prepare a granulated particle for cold storage material particle having a particle diameter of 0.4 mm to 0.6 mm. At this time, polyvinyl alcohol was used as a binder, and added in an amount of 1.2 wt % with respect to the raw material powders. The carbon concentration of the granulated particle for cold storage material particle was 0.99 wt %. The relative density of the granulated particle for cold storage material particle was 34%.

In order to evaluate the strength of the granulated particle for cold storage material particle, the granulated particle was filled in a cylindrical container having a diameter of @15 mm and a height of 5 mm. At this time, the granulated particle for cold storage material particle was filled in a sufficient amount so that the granulated particle for cold storage material particle was fixed in the cylindrical container to prevent the granulated particle for cold storage material particle from moving freely. A single vibration having an amplitude of 2 mm and a maximum acceleration of 200 $m/s^2$ was applied to the container $1\times10^3$ times. As a result, the proportion of the broken granulated particle for cold storage material particle was less than 0.1 wt %.

The granulated particle for cold storage material particle was degreased at 600° C. for 2 hours in an air atmosphere. The degreased granulated particle for cold storage material particle had a carbon concentration of 0.51 wt % and a relative density of 40%. The granulated particle for cold storage material particle was subjected to a heat treatment at 600° C. for 2 hours in an atmosphere containing hydrogen sulfide ($H_2S$) for sulfurize the granulated particle. Thereafter, the granulated particle for cold storage material particle was subjected to a heat treatment at 1300° C. for 12 hours in an inert gas atmosphere to sinter the granulated particle for cold storage material particle, thereby producing a cold storage material particle.

The main component of the cold storage material particle in Example 1 is a gadolinium oxysulfide.

In the following examples and comparative examples, a time for which raw material powders are mixed, a condition for the heat treatment for degreasing, a condition for the heat treatment for sulfurization, a condition for the heat treatment for sintering, etc. are adjusted to be appropriate conditions.

Example 2

A granulated particle for cold storage material particle and a cold storage material particle were produced in the same manner as in Example 1, except that a mixture of $Gd_2O_3$ powders and $Na_2CO_3$ powders was used as raw material powders.

Example 3

A granulated particle for cold storage material particle and a cold storage material particle were produced in the same manner as in Example 2, except that $K_2CO_3$ powders were used instead of the $Na_2CO_3$ powders.

Example 4

A granulated particle for cold storage material particle and a cold storage material particle were produced in the same manner as in Example 2, except that $CaCO_3$ powders were used instead of the $Na_2CO_3$ powders.

Example 5

A granulated particle for cold storage material particle and a cold storage material particle were produced in the same manner as in Example 2, except that $MgCO_3$ powders were used instead of the $Na_2CO_3$ powders.

Example 6

A granulated particle for cold storage material particle and a cold storage material particle were produced in the same manner as in Example 2, except that $SrCO_3$ powders were used instead of the $Na_2CO_3$ powders.

Example 7

A granulated particle for cold storage material particle and a cold storage material particle were produced in the same manner as in Example 2, except that $CaCO_3$ powders were used in addition to the $Na_2CO_3$ powders.

Example 8

A granulated particle for cold storage material particle and a cold storage material particle were produced in the same manner as in Example 7, except that $MgCO_3$ powders were used instead of the $CaCO_3$ powders.

Example 9

A granulated particle for cold storage material particle and a cold storage material particle were produced in the same manner as in Example 7, except that $SrCO_3$ powders were used instead of the $CaCO_3$ powders.

Example 10

A granulated particle for cold storage material particle and a cold storage material particle were produced in the same manner as in Example 1, except that $Ho_2O_3$ powders were used instead of the $Gd_2O_3$ powders.

Example 11

A granulated particle for cold storage material particle and a cold storage material particle were produced in the same manner as in Example 2, except that $K_2CO_3$ powders were used in addition to the $Na_2CO_3$ powders.

Example 12

A granulated particle for cold storage material particle and a cold storage material particle were produced in the same manner as in Example 2, except that $K_2CO_3$ powders and $CaCO_3$ powders were used in addition to the $Na_2CO_3$ powders.

Examples 13 to 15

A granulated particle for cold storage material particle and a cold storage material particle were produced in the same manner as in Example 2, except that the weight of the $Na_2CO_3$ powders was changed.

Examples 16 to 18

A granulated particle for cold storage material particle and a cold storage material particle were produced in the same manner as in Example 7, except that the weight of the $CaCO_3$ powders was changed.

Example 19

A granulated particle for cold storage material particle and a cold storage material particle were produced in the same manner as in Example 2, except that some of the $Gd_2O_3$ powders were changed to $HO_2O_3$.

Example 20

A granulated particle for cold storage material particle and a cold storage material particle were produced in the same manner as in Example 1, except that $Gd_2O_2S$ powders were used instead of the $Gd_2O_3$ powders and sulfurization was not performed.

Example 21

A slurry was prepared by adding $Gd_2O_3$ powders to a sodium alginate aqueous solution and mixing them for 24 hours. The weight ratio of the raw material powders to the alginate aqueous solution was 0.5 times. The prepared slurry was added dropwise into a calcium lactate aqueous solution as a gelling solution. A syringe was used for dropping the slurry.

The diameter of the syringe was 510 μm, and the distance from the tip of the syringe to the liquid level of the calcium lactate aqueous solution was 100 mm. The slurry dropped with the syringe was held in the gelling solution for 5 hours.

Thereafter, the gelled granulated particle for cold storage material particle was washed with pure water. After being washed, the granulated particle for cold storage material particle was dried. The granulated particle for cold storage material particle had a sodium concentration of 0.83 atom % and a carbon concentration of 0.5 wt %. The granulated particle for cold storage material particle had a relative density of 27%. After being dried, the granulated particle for cold storage material particle was degreased, sulfurized, and sintered.

The granulated particle for cold storage material particle was degreased at 500° C. for 2 hours in an air atmosphere. After being degreased, the granulated particle for cold storage material particle had a sodium concentration of 1.0 atom %, a carbon concentration of 0.25 wt %, and a relative density of 30%. After being degreased, the granulated particle for cold storage material particle was subjected to a heat treatment at 600° C. for 2 hours in an atmosphere containing hydrogen sulfide ($H_2S$) to sulfurize the granulated particle for cold storage material particle. The granulated particle for cold storage material particle was subjected to a heat treatment at 1300° C. for 12 hours in an inert gas atmosphere to sinter the granulated particle for cold storage material particle, thereby producing a cold storage material particle.

The main component of the cold storage material particle in Example 21 is a gadolinium oxysulfide. The sodium concentration in the cold storage material particle in Example 21 was 1.1 atom %.

Examples 22 to 24

A granulated particle for cold storage material particle and a cold storage material particle were produced in the same manner as in Example 21, except that the relative density of the granulated particle for cold storage material particle was changed by changing the ratio of the raw material powders and the sodium alginate aqueous solution, and sodium and calcium were removed by changing the washing time and the number of times.

Examples 25 and 26

A granulated particle for cold storage material particle and a cold storage material particle were produced in the same manner as in Example 21, except that the concentration of carbon contained in the granulated particle for cold storage material particle was changed by changing the concentration of the sodium alginate aqueous solution, and the washing time was adjusted.

Example 27

A granulated particle for cold storage material particle and a cold storage material particle were produced in the same manner as in Example 21, except that a magnesium chloride aqueous solution was used instead of the calcium lactate aqueous solution.

Example 28

A granulated particle for cold storage material particle and a cold storage material particle were produced in the same manner as in Example 21, except that a strontium chloride aqueous solution was used instead of the calcium lactate aqueous solution.

Example 29

A granulated particle for cold storage material particle and a cold storage material particle were produced in the same manner as in Example 21, except that an air-pulse dispenser was used rather than the syringe as a slurry dropping method. The diameter of the nozzle was 510 μm, and the distance from the tip of the nozzle to the liquid level of the calcium lactate aqueous solution was 100 mm.

Example 30

A granulated particle for cold storage material particle and a cold storage material particle were produced in the same manner as in Example 21, except that a piezo dispenser was used rather than the syringe as a slurry dropping method. The diameter of the nozzle was 510 μm, and the distance from the tip of the nozzle to the liquid level of the calcium lactate aqueous solution was 100 mm.

Example 31

A granulated particle for cold storage material particle and a cold storage material particle were produced in the same manner as in Example 21, except that a continuous type inkjet was used rather than the syringe as a slurry dropping method.

Examples 32 to 37

The granulated particles for cold storage material particles and the cold storage material particles in Examples 32 to 37 are different in particle diameter or aspect ratio from the granulated particle for cold storage material particle and the cold storage material particle in Example 21. When the granulated particles for cold storage material particles in Examples 32 to 37 were produced, the diameter of the syringe and the distance from the tip of the syringe to the surface of the gelling solution were changed as compared with those when the granulated particle for cold storage material particle was produced in Example 21.

Example 38

A granulated particle for cold storage material particle and a cold storage material particle were produced in the same manner as in Example 21, except that the relative density was set to 11% by changing the ratio between the raw material powders and the sodium alginate aqueous solution, and only calcium was removed by changing the immersion time, the washing time, and the number of times.

Example 39

A granulated particle for cold storage material particle and a cold storage material particle were produced in the same manner as in Example 21, except that the relative density was set to 11% by changing the ratio between the raw material powders and the sodium alginate aqueous solution, and only sodium was removed by changing the immersion time, the washing time, and the number of times.

Example 40

A granulated particle for cold storage material particle and a cold storage material particle were produced in the same manner as in Example 22, except that $Al_2O_3$ powders were also used as the raw material powders. The $Al_2O_3$ powders were added so that the cold storage material particle contained 15 atom % of Al.

Example 41

A granulated particle for cold storage material particle and a cold storage material particle were produced in the same manner as in Example 38, except that $Al_2O_3$ powders were also used as the raw material powders. The $Al_2O_3$ powders were added so that the cold storage material particle contained 15 atom % of Al.

Example 42

A granulated particle for cold storage material particle and a cold storage material particle were produced in the same manner as in Example 21 except that the relative density was set to 11% by changing the ratio between the raw material powders and the sodium alginate aqueous solution, and $Al_2O_3$ powders were also used as the raw material powders. The $Al_2O_3$ powders were added so that the cold storage material particle contained 15 atom % of Al.

Example 43

A granulated particle for cold storage material particle and a cold storage material particle were produced in the same manner as in Example 21 except that the relative density was set to 11% by changing the ratio between the raw material powders and the sodium alginate aqueous solution, and an aluminum chloride aqueous solution was used instead of the calcium lactate aqueous solution. The aluminum chloride aqueous solution was used in such a manner that Al was contained in an amount of 0.01 atom % in the cold storage material particle.

Example 44

A granulated particle for cold storage material particle and a cold storage material particle were produced in the same manner as in Example 21 except that the relative density was set to 11% by changing the ratio between the raw material powders and the sodium alginate aqueous solution, and an aluminum chloride aqueous solution was used in addition to the calcium lactate aqueous solution. The aluminum chloride aqueous solution was used in such a manner that Al was contained in an amount of 0.01 atom % in the cold storage material particle.

Example 45

A granulated particle for cold storage material particle and a cold storage material particle were produced in the same manner as in Example 21 except that the relative density was set to 11% by changing the ratio between the raw material powders and the sodium alginate aqueous solution, and an aluminum chloride aqueous solution was used in addition to the calcium lactate aqueous solution. The aluminum chloride aqueous solution was added in such a manner that Al was contained in an amount of 20 atom % in the cold storage material particle.

Example 46

A granulated particle for cold storage material particle and a cold storage material particle were produced in the same manner as in Example 1 except that $Gd_2O_3$ powders and $Al_2O_3$ powders were used as the raw material powders, and a heat treatment was not performed in an atmosphere containing hydrogen sulfide ($H_2S$). The main component of the cold storage material particle is $GdAlO_3$.

Example 47

A granulated particle for cold storage material particle and a cold storage material particle were produced in the same manner as in Example 2 except that $Gd_2O_3$ powders and $Al_2O_3$ powders were used as the raw material powders, and a heat treatment was not performed in an atmosphere containing hydrogen sulfide ($H_2S$). The main component is $GdAlO_3$.

Example 48

A granulated particle for cold storage material particle and a cold storage material particle were produced in the same manner as in Example 21 except that $Gd_2O_3$ powders and $Al_2O_3$ powders were used as the raw material powders, and a heat treatment was not performed in an atmosphere containing hydrogen sulfide ($H_2S$). The main component is $GdAlO_3$.

Comparative Example 1

A granulated particle for cold storage material particle in Comparative Example 1 is different from the granulated particle for cold storage material particle in Example 21 in that the relative density is 9%, which is smaller than that in Example 21. When the granulated particle for cold storage material particle were produced in Comparative Example 1, the amount of the raw material powders was reduced as compared with that when the granulated particle for cold storage material particle was produced in Example 21.

Comparative Example 2

A granulated particle for cold storage material particle in Comparative Example 2 is different from the granulated particle for cold storage material particle in Example 21 in that the relative density is 51%, which is larger than that in Example 21. When the granulated particle for cold storage material particle was produced in Comparative Example 2, the weight of the raw material powders was increased as compared with that when the granulated particle for cold storage material particle was produced in Example 21.

Comparative Example 3

A granulated particle for cold storage material particle in Comparative Example 3 is different from the granulated particle for cold storage material particle in Example 21 in that the carbon concentration is 0.0004 wt %, which is smaller than that in Example 21. When the granulated particle for cold storage material particle was produced in Comparative Example 3, the concentration of the sodium alginate aqueous solution was reduced as compared with that when the granulated particle for cold storage material particle was produced in Example 21.

Comparative Example 4

A granulated particle for cold storage material particle in Comparative Example 4 is different from the granulated particle for cold storage material particle in Example 21 in that the carbon concentration is 51 wt %, which is larger than that in Example 21. When the granulated particle for cold storage material particle was produced in Comparative Example 4, the concentration of the sodium alginate aqueous solution was increased as compared with that when the granulated particle for cold storage material particle was produced in Example 21.

Comparative Example 5

A granulated particle for cold storage material particle and a cold storage material particle in Comparative Example 5 are different from those in Example 41 in that Al contained in the cold storage material particle is 65 atom %, which is larger than that in Example 41. When the granulated particle for cold storage material particle and the cold storage material particles were produced in Comparative Example 5, the weight of the Al 03 powders was increased as compared with that when the granulated particle for cold storage material particle and the cold storage material particles were produced in Example 41.

For the granulated particle for cold storage material particle and the cold storage material particle according to each of the examples and the comparative examples, the strength of the granulated particle for cold storage material particle and the relative density and the specific heat of the cold storage material particle were measured. The results are shown in Table 1, Table 2, and Table 3. In Table 1, the granulated particle for cold storage material particle is referred to as "granulated particle", and the cold storage material particle produced from the granulated particle for cold storage material particle is referred to as "cold storage material particle".

TABLE 1

| | granulation method | oxysulfide/ oxide phase | relative density of granulated particle (%) | carbon concen-tration of granulated particle (wt %) | Group 1 element | concen-tration of Group 1 element in particle (atom %) | Group 2 element | concen-tration of Group 2 element in particle (atom %) | additive element |
|---|---|---|---|---|---|---|---|---|---|
| Example 1 | tumbling granulation | Gd2O2S | 34 | 0.99 | | | | | |
| Example 2 | tumbling granulation | Gd2O2S | 34 | 0.99 | Na | 0.55% | | | |
| Example 3 | tumbling granulation | Gd2O2S | 34 | 0.99 | K | 0.87% | | | |
| Example 4 | tumbling granulation | Gd2O2S | 34 | 0.99 | | | Ca | 0.004% | |
| Example 5 | tumbling granulation | Gd2O2S | 34 | 0.99 | | | Mg | 0.010% | |
| Example 6 | tumbling granulation | Gd2O2S | 34 | 0.99 | | | Sr | 0.012% | |
| Example 7 | tumbling granulation | Gd2O2S | 34 | 0.99 | Na | 0.59% | Ca | 0.004% | |
| Example 8 | tumbling granulation | Gd2O2S | 34 | 0.99 | Na | 0.43% | Mg | 0.010% | |
| Example 9 | tumbling granulation | Gd2O2S | 34 | 0.99 | Na | 0.41% | Sr | 0.012% | |
| Example 10 | tumbling granulation | Ho2O2S | 34 | 0.99 | | | | | |
| Example 11 | tumbling granulation | Gd2O2S | 34 | 0.99 | Na<br>K | 0.76%<br>0.82% | | | |
| Example 12 | tumbling granulation | Gd2O2S | 34 | 0.99 | Na<br>K | 0.62%<br>0.64% | Ca | 0.16% | |
| Example 13 | tumbling granulation | Gd2O2S | 34 | 0.99 | Na | 0.01% | | | |
| Example 14 | tumbling granulation | Gd2O2S | 34 | 0.99 | Na | 0.002% | | | |
| Example 15 | tumbling granulation | Gd2O2S | 34 | 0.99 | Na | 9.80% | | | |
| Example 16 | tumbling granulation | Gd2O2S | 34 | 0.99 | Na | 0.59% | Ca | 0.003% | |
| Example 17 | tumbling granulation | Gd2O2S | 34 | 0.99 | Na | 0.59% | Ca | 0.001% | |
| Example 18 | tumbling granulation | Gd2O2S | 34 | 0.99 | Na | 0.59% | Ca | 9.90% | |
| Example 19 | tumbling granulation | (Gd, Ho)2O2S | 34 | 0.99 | Na | 0.55% | | | |
| Example 20 | tumbling granulation | Gd2O2S | 34 | 0.99 | | | | | |

| | concen-tration of additive element in particle (atom %) | Particle size of granulated particle (μm) | aspect ratio of granulated particle | particle size of cold storage material particle (μm) | aspect ratio of cold storage material particle | destruction rate of granulated particle | relative density of cold storage material particle | maximum value of volume specific heat at 20 K or lower ($J/cm^3 \cdot K$) |
|---|---|---|---|---|---|---|---|---|
| Example 1 | | 360 | 1.3 | 250 | 1.1 | less than 0.1 wt % | 99.0% | 1.20 |
| Example 2 | | 360 | 1 | 250 | 1 | less than 0.1 wt % | 99.0% | 1.20 |
| Example 3 | | 370 | 1 | 260 | 1 | less than 0.1 wt % | 99.0% | 1.20 |
| Example 4 | | 360 | 1.3 | 250 | 1 | less than 0.1 wt % | 99.0% | 1.20 |
| Example 5 | | 360 | 1.3 | 250 | 1 | less than 0.1 wt % | 99.0% | 1.20 |
| Example 6 | | 360 | 1.3 | 250 | 1 | less than 0.1 wt % | 99.0% | 1.20 |
| Example 7 | | 630 | 1.1 | 440 | 1.1 | less than 0.1 wt % | 99.0% | 1.20 |
| Example 8 | | 515 | 1 | 360 | 1 | less than 0.1 wt % | 99.0% | 1.20 |
| Example 9 | | 660 | 1.5 | 460 | 1.5 | less than 0.1 wt % | 99.0% | 1.20 |
| Example 10 | | 645 | 1 | 450 | 1 | less than 0.1 wt % | 99.0% | 1.25 |
| Example 11 | | 504 | 1 | 352 | 1 | less than 0.1 wt % | 99.0% | 1.20 |

TABLE 1-continued

| | | | | | | | |
|---|---|---|---|---|---|---|---|
| Example 12 | 603 | 1.2 | 421 | 1.2 | less than 0.1 wt % | 99.0% | 1.20 |
| Example 13 | 358 | 1 | 250 | 1 | less than 0.1 wt % | 99.0% | 1.20 |
| Example 14 | 344 | 1 | 240 | 1 | less than 0.1 wt % | 99.0% | 1.20 |
| Example 15 | 348 | 1 | 243 | 1 | less than 0.1 wt % | 99.0% | 0.90 |
| Example 16 | 630 | 1.1 | 440 | 1.1 | less than 0.1 wt % | 99.0% | 1.20 |
| Example 17 | 616 | 1.1 | 430 | 1.1 | less than 0.1 wt % | 99.0% | 1.20 |
| Example 18 | 630 | 1.1 | 440 | 1.1 | less than 0.1 wt % | 99.0% | 0.90 |
| Example 19 | 430 | 1 | 300 | 1 | less than 0.1 wt % | 99.0% | 1.10 |
| Example 20 | 360 | 1.3 | 250 | 1.1 | less than 0.1 wt % | 99.0% | 1.20 |

TABLE 2

| | granulation method | oxysulfide/ oxide phase | relative density of granulated particle (%) | carbon concen- tration of granulated particle (wt %) | Group 1 element | concen- tration of Group 1 element in particle (atom %) | Group 2 element | concen- tration of Group 2 element in particle (atom %) | additive element |
|---|---|---|---|---|---|---|---|---|---|
| Example 21 | syringe dropping | Gd2O2S | 27 | 0.5 | Na | 0.83% | Ca | 0.16% | |
| Example 22 | syringe dropping | Gd2O2S | 11 | 0.5 | | | | | |
| Example 23 | syringe dropping | Gd2O2S | 16 | 0.5 | | | | | |
| Example 24 | syringe dropping | Gd2O2S | 47 | 0.5 | | | | | |
| Example 25 | syringe dropping | Gd2O2S | 27 | 0.006 | Na | 0.0008% | Ca | 0.23% | |
| Example 26 | syringe dropping | Gd2O2S | 27 | 28 | Na | 5.10% | Ca | 0.82% | |
| Example 27 | syringe dropping | Gd2O2S | 27 | 0.5 | Na | 0.79% | Mg | 0.21% | |
| Example 28 | syringe dropping | Gd2O2S | 27 | 0.5 | Na | 0.95% | Sr | 0.91% | |
| Example 29 | air-pulse dispenser | Gd2O2S | 27 | 0.5 | Na | 0.95% | Ca | 0.16% | |
| Example 30 | piezo dispenser | Gd2O2S | 27 | 0.5 | Na | 0.92% | Ca | 0.18% | |
| Example 31 | continuous type inkjet | Gd2O2S | 27 | 0.5 | Na | 0.95% | Ca | 0.16% | |
| Example 32 | syringe dropping | Gd2O2S | 27 | 0.5 | Na | 0.95% | Ca | 0.16% | |
| Example 33 | syringe dropping | Gd2O2S | 27 | 0.5 | Na | 0.95% | Ca | 0.16% | |
| Example 34 | syringe dropping | Gd2O2S | 27 | 0.5 | Na | 0.95% | Ca | 0.16% | |
| Example 35 | syringe dropping | Gd2O2S | 27 | 0.5 | Na | 0.95% | Ca | 0.16% | |
| Example 36 | syringe dropping | Gd2O2S | 27 | 0.5 | Na | 0.95% | Ca | 0.16% | |
| Example 37 | syringe dropping | Gd2O2S | 27 | 0.5 | Na | 0.95% | Ca | 0.16% | |
| Example 38 | syringe dropping | Gd2O2S | 11 | 0.5 | Na | 0.01% | | | |
| Example 39 | syringe dropping | Gd2O2S | 11 | 0.5 | | | Ca | 0.02% | |
| Example 40 | syringe dropping | Gd2O2S | 11 | 0.5 | | | | | Al |
| Example 41 | syringe dropping | Gd2O2S | 11 | 0.5 | Na | 0.009% | | | Al |
| Example 42 | syringe dropping | Gd2O2S | 11 | 0.5 | Na | 0.011% | Ca | 0.16% | Al |
| Example 43 | syringe dropping | Gd2O2S | 11 | 0.5 | Na | 0.01% | | | Al |
| Example 44 | syringe dropping | Gd2O2S | 11 | 0.5 | Na | 0.83% | Ca | 0.16% | Al |

TABLE 2-continued

| | | | | | | | | | |
|---|---|---|---|---|---|---|---|---|---|
| Example 45 | syringe dropping | Gd2O2S | 11 | 0.5 | Na | 0.011% | Ca | 0.16% | Al |

| | concentration of additive element in particle (atom %) | Particle size of granulated particle (μm) | aspect ratio of granulated particle | particle size of cold storage material particle (μm) | aspect ratio of cold storage material particle | destruction rate of granulated particle | relative density of cold storage material particle | maximum value of volume specific heat at 20 K or lower ($J/cm^3 \cdot K$) |
|---|---|---|---|---|---|---|---|---|
| Example 21 | | 511 | 1.1 | 330 | 1.1 | less than 0.1 wt % | 99.0% | 1.20 |
| Example 22 | | 522 | 1.3 | 250 | 1.1 | 0.99 wt % | 95.0% | 1.15 |
| Example 23 | | 461 | 1.3 | 250 | 1.1 | 0.14 wt % | 99.0% | 1.20 |
| Example 24 | | 322 | 1.3 | 250 | 1.1 | less than 0.1 wt % | 99.0% | 1.20 |
| Example 25 | | 387 | 1.3 | 250 | 1.1 | 0.98 wt % | 95.0% | 1.15 |
| Example 26 | | 387 | 1.3 | 250 | 1.1 | less than 0.1 wt % | 95.0% | 1.15 |
| Example 27 | | 681 | 1 | 440 | 1 | less than 0.1 wt % | 99.0% | 1.20 |
| Example 28 | | 603 | 1.3 | 390 | 1.3 | less than 0.1 wt % | 99.0% | 1.20 |
| Example 29 | | 545 | 1 | 352 | 1 | less than 0.1 wt % | 99.0% | 1.20 |
| Example 30 | | 396 | 1.1 | 256 | 1.1 | less than 0.1 wt % | 99.0% | 1.20 |
| Example 31 | | 464 | 1.3 | 300 | 1 | less than 0.1 wt % | 99.0% | 1.20 |
| Example 32 | | 77 | 1 | 50 | 1 | less than 0.1 wt % | 99.0% | 1.20 |
| Example 33 | | 4642 | 1 | 3000 | 1 | less than 0.1 wt % | 99.0% | 1.20 |
| Example 34 | | 62 | 1 | 40 | 1 | less than 0.1 wt % | 99.0% | 1.20 |
| Example 35 | | 6189 | 1 | 4000 | 1 | less than 0.1 wt % | 99.0% | 1.20 |
| Example 36 | | 387 | 4.8 | 250 | 4.8 | less than 0.1 wt % | 99.0% | 1.20 |
| Example 37 | | 387 | 5.5 | 250 | 5.5 | less than 0.1 wt % | 99.0% | 1.20 |
| Example 38 | | 522 | 1.3 | 250 | 1.1 | 0.99 wt % | 99.0% | 1.20 |
| Example 39 | | 522 | 1.3 | 250 | 1.1 | 0.99 wt % | 99.0% | 1.20 |
| Example 40 | 15% | 522 | 1.3 | 250 | 1.1 | 0.99 wt % | 99.5% | 0.80 |
| Example 41 | 15% | 522 | 1.3 | 250 | 1.1 | 0.99 wt % | 99.6% | 0.80 |
| Example 42 | 15% | 689 | 1.1 | 330 | 1.1 | less than 0.1 wt % | 99.8% | 0.80 |
| Example 43 | 0.010% | 689 | 1.1 | 330 | 1.1 | less than 0.1 wt % | 99.6% | 1.20 |
| Example 44 | 0.010% | 689 | 1.1 | 330 | 1.1 | less than 0.1 wt % | 99.8% | 1.20 |
| Example 45 | 20% | 689 | 1.1 | 330 | 1.1 | less than 0.1 wt % | 99.8% | 0.75 |

TABLE 3

| | granulation method | oxysulfide/ oxide phase | relative density of granulated particle (%) | carbon concentration of granulated particle (wt %) | Group 1 element | concentration of Group 1 element in particle (atom %) | Group 2 element | concentration of Group 2 element in particle (atom %) | additive element |
|---|---|---|---|---|---|---|---|---|---|
| Example 46 | tumbling granulation | GdAlO3 | 30 | 0.99 | | | | | |
| Example 47 | tumbling granulation | GdAlO3 | 30 | 0.99 | Na | 0.55% | | | |

TABLE 3-continued

| | | | | | | | | | |
|---|---|---|---|---|---|---|---|---|---|
| Example 48 | syringe dropping | GdAlO3 | 25 | 0.5 | Na | 0.83% | Ca | 0.16% | |
| Comparative Example 1 | syringe dropping | Gd2O2S | 9 | 0.5 | Na | 0.83% | Ca | 0.16% | |
| Comparative Example 2 | syringe dropping | Gd2O2S | 51 | 0.5 | Na | 0.83% | Ca | 0.16% | |
| Comparative Example 3 | syringe dropping | Gd2O2S | 27 | 0.0004 | Na | 0.00% | Ca | 0.19% | |
| Comparative Example 4 | syringe dropping | Gd2O2S | 27 | 51 | Na | 8.90% | Ca | 1.50% | |
| Comparative Example 5 | syringe dropping | Gd2O2S | 11 | 0.5 | Na | 0.009% | | | Al |

| | concentration of additive element in particle (atom %) | Particle size of granulated particle (μm) | aspect ratio of granulated particle | particle size of cold storage material particle (μm) | aspect ratio of cold storage material particle | destruction rate of granulated particle | relative density of cold storage material particle | maximum value of volume specific heat at 20 K or lower (J/cm³ · K) |
|---|---|---|---|---|---|---|---|---|
| Example 46 | | 360 | 1.3 | 250 | 1.1 | less than 0.1 wt % | 99.0% | 0.90 |
| Example 47 | | 360 | 1 | 250 | 1 | less than 0.1 wt % | 99.0% | 0.90 |
| Example 48 | | 511 | 1.1 | 330 | 1.1 | less than 0.1 wt % | 99.0% | 0.90 |
| Comparative Example 1 | | 736 | 1.1 | 330 | 1.1 | | | |
| Comparative Example 2 | | 413 | 1.1 | 330 | 1.1 | less than 0.1 wt % | 40.8% | 0.49 |
| Comparative Example 3 | | 511 | 1.1 | 330 | 1.1 | | | |
| Comparative Example 4 | | 511 | 1.1 | 330 | 1.1 | less than 0.1 wt % | 40.8% | 0.49 |
| Comparative Example 5 | 65% | 522 | 1.3 | 250 | 1.1 | 0.99 wt % | 99.9% | 0.30 |

As in Comparative Example 1, when the relative density of the granulated particle for cold storage material particle is less than 10%, the granulated particle cannot be recovered as a spherical particle. This is considered to be because, when the relative density was less than 10%, the proportion of voids contained in the granulated particle for cold storage material particle was large, and accordingly, the strength of the granulated particle for cold storage material particle was significantly reduced.

As in Comparative Example 2, when the relative density of the granulated particle for cold storage material particle exceeded 50%, the relative density of the produced cold storage material particle was significantly reduced, and the specific heat of the produced cold storage material particle was also significantly reduced. This is considered to be because, when the relative density of the granulated particle for cold storage material particle exceeded 50%, the organic component contained in the granulated particle for cold storage material particle was not sufficiently removed, and accordingly, the sinterability of the cold storage material particle was impaired.

According to the result of Comparative Example 3, when the carbon concentration of the granulated particle for cold storage material particle is less than 0.001 wt %, the strength of the granulated particle for cold storage material particle decreases. For this reason, the granulated particle for cold storage material particle is easily broken when handled, and the yield is remarkably lowered.

According to the result of Comparative Example 4, when the carbon concentration of the granulated particle for cold storage material particle exceeds 50 wt %, the relative density of the cold storage material particle after sintering is significantly reduced, and the specific heat of the cold storage material particle after sintering is also significantly reduced. This is considered to be because the organic component contained in the granulated particle was not sufficiently removed and a large amount of carbon remained, and accordingly, the sinterability of the cold storage material particle was impaired.

It can be seen from Examples 22 to 24 that the relative density of the cold storage material particle is improved and the specific heat of the cold storage material particle is also improved in a case where the granulated particle does not contain a Group 1 element or a Group 2 element and has a relative density of 15% or more and 50% or less as compared with those in a case where the granulated particle has a relative density of 10% or more and 15% or less. This is considered to be because, when the relative density is too low, the number of contact points between the raw material powders decreases, and the sinterability of the cold storage material particle decreases.

It can be seen from Examples 38 and 39 that, in a case where the granulated particle contains a Group 1 element or a Group 2 element, the relative density of the cold storage material particle is improved and the specific heat of the cold storage material particle is also improved even when the granulated particle has a relative density of 10% or more and 15% or less. This is considered to be due to the sintering promoting effect of the Group 1 element and the Group 2 element.

Through Examples 40 to 45, it can be seen that even when the granulated particle has a relative density of 10% or more and 15% or less, if the granulated particle contains a sintering aid, the relative density of the sintered particle is improved. This is considered to be due to the sintering promoting effect of the sintering aid. In a case where the granulated particle has a relative density of less than 10%, even when the granulated particle contain a sintering aid, the relative density of the cold storage material particle decreases and the specific heat of the cold storage material particle also decreases.

According to the result of Comparative Example 5, it can be seen that, in a case where the atomic concentration of the additive element derived from the sintering aid is so large as to exceed 60 atom %, the specific heat of the cold storage material particle decreases.

Through Examples 46 to 48, it can be seen that, by not performing a heat treatment in a hydrogen sulfide atmosphere, even when the main component of the cold storage material particle is $GdAlO_3$, if the granulated particle for cold storage material particle has a relative density of 10% or more and 50% or less, the same effect as when the main component is gadolinium oxysulfide is exhibited.

From the above examples, the effects exhibited by the granulated particle for cold storage material particle according to the first embodiment and the cold storage material particle according to the second embodiment were confirmed.

Although the air-pulse dispenser or the piezo dispenser has been described as an example of the dispenser, a plunger dispenser may be used.

Although the continuous type inkjet has been described as an example of the inkjet, an on-demand type inkjet may be used.

Although some embodiments of the present invention have been described, these embodiments are exemplary, and are not intended to limit the scope of the invention. These novel embodiments can be implemented in various other forms, and various omissions, substitutions, and changes can be made without departing from the gist of the invention. For example, a component of one embodiment may be replaced or changed with a component of another embodiment. These embodiments and modifications thereof fall within the scope and gist of the invention, and fall within the scope of the equivalent to the invention set forth in the claims.

What is claimed is:

1. A granulated particle for cold storage material particle, the granulated particle comprising:

a rare earth oxysulfide containing at least one rare earth element selected from the group consisting of Y, La, Ce, Pr, Nd, Sm, Eu, Gd, Tb, Dy, Ho, Er, Tm, Yb, and Lu, or a rare earth oxide containing at least one rare earth element selected from the group consisting of Y, La, Ce, Pr, Nd, Sm, Eu, Gd, Tb, Dy, Ho, Er, Tm, Yb, and Lu; and carbon having a concentration of 0.001 wt % or more and 50 wt % or less, wherein the granulated particle has a relative density of 10% or more and 50% or less.

2. The granulated particle for cold storage material particle according to claim 1, wherein the granulated particle has a particle diameter of 50 μm or more and 7 mm or less.

3. The granulated particle for cold storage material particle according to claim 1, wherein the granulated particle has an aspect ratio of 1 or more and 5 or less.

4. The granulated particle for cold storage material particle according to claim 1, further comprising a Group 1 element having a concentration of 0.001 atom % or more and 60 atom % or less.

5. The granulated particle for cold storage material particle according to claim 4, wherein the Group 1 element is at least one element selected from the group consisting of Li, Na, and K.

6. The granulated particle for cold storage material particle according to claim 1, further comprising a Group 2 element having a concentration of 0.001 atom % or more and 60 atom % or less.

7. The granulated particle for cold storage material particle according to claim 6, wherein the Group 2 element is at least one element selected from the group consisting of Mg, Ca, Sr, and Ba.

8. The granulated particle for cold storage material particle according to claim 1, further comprising an additive element having a concentration of 0.001 atom % or more and 60 atom % or less, the additive element being at least one element selected from the group consisting of Mn, Al, Fe, Cu, Ni, Co, Zr, Y, and B.

9. The granulated particle for cold storage material particle according to claim 1, wherein the granulated particle is a gel.

10. A cold storage material particle obtained by sintering the granulated particle for cold storage material particle according to claim 1.

11. The cold storage material particle according to claim 10, wherein a maximum value of a volume specific heat in a temperature range of 2 K or more and 10 K or less is 0.5 $J/(cm^3 \cdot K)$ or more.

12. The cold storage material particle according to claim 10, wherein the cold storage material particle has a particle diameter of 50 μm or more and 5 mm or less.

13. The cold storage material particle according to claim 10, wherein the cold storage material particle has an aspect ratio of 1 or more and 5 or less.

14. A cold storage device filled with a plurality of the cold storage material particles according to claim 10.

15. A refrigerator comprising the cold storage device according to claim 14.

16. A cryopump comprising the refrigerator according to claim 15.

17. A superconducting magnet comprising the refrigerator according to claim 15.

18. A nuclear magnetic resonance imaging apparatus comprising the refrigerator according to claim 15.

19. A nuclear magnetic resonance apparatus comprising the refrigerator according to claim 15.

20. A magnetic field application single crystal pulling apparatus comprising the refrigerator according to claim 15.

21. A helium re-condensing device comprising the refrigerator according to claim 15.

* * * * *